United States Patent [19]

Blattner et al.

[11] Patent Number: 4,707,476

[45] Date of Patent: Nov. 17, 1987

[54] TREATING STATES OF AGITATION WITH AZATETRACYCLIC COMPOUNDS

[75] Inventors: Hans Blattner, Riehen; Angelo Storni, Rheinfelden, both of Switzerland

[73] Assignee: Ciba-Geigy Corporation, Ardsley, N.Y.

[21] Appl. No.: 191,728

[22] Filed: Sep. 29, 1980

Related U.S. Application Data

[63] Continuation of Ser. No. 961,324, Nov. 17, 1978, abandoned, which is a continuation-in-part of Ser. No. 798,204, May 18, 1977, abandoned.

[51] Int. Cl.$^4$ .................... A61K 31/55; C07D 487/04
[52] U.S. Cl. .................................. 514/215; 514/213; 540/576; 540/578; 540/580
[58] Field of Search .................... 260/330.3, 330.9; 424/244; 540/576, 578, 580; 514/213, 215

[56] References Cited

U.S. PATENT DOCUMENTS 4,002,632  1/1977  van der Burg .................... 546/70
4,187,314  2/1980  Holden et al. .................... 514/213

Primary Examiner—Richard A. Schwartz
Attorney, Agent, or Firm—Michael W. Glynn; Irving M. Fishman

[57] ABSTRACT

Azatetracyclic compounds of the formula

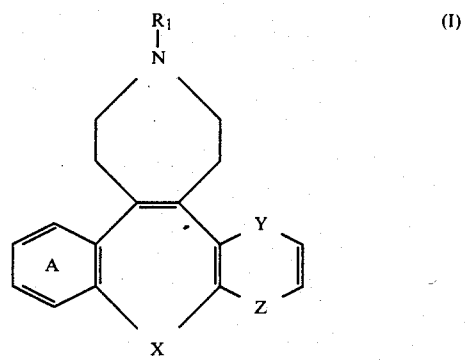

wherein the various substituents are defined hereinbelow.

The novel compounds can be used as tranquillizing, antipsychotic and excitation-inhibiting compounds for the treatment of states of agitation. Specific embodiments are 3-methyl-2,3,4,5-tetrahydro-1H-dibenzo[2,3:6,7]thiepino[4,5-d]azepine and 3-methyl-2,3,4,5-tetrahydro-1H-dibenzo[2,3:6,7]oxepino[4,5-d]azepine.

15 Claims, No Drawings

TREATING STATES OF AGITATION WITH AZATETRACYCLIC COMPOUNDS

This is a continuation of application Ser. No. 961,324, filed on Nov. 17, 1978, now abandoned, which is a continuation-in-part of our application Ser. No. 798,204, filed May 18, 1977, now abandoned.

The present invention relates to novel azatetracyclic compounds and their acid addition salts having useful pharmacological properties, a process for their manufacture, and also to pharmaceutical compositions which contain the novel compounds as active ingredient, and to their use.

The azatetracyclic compounds of the present invention have the formula

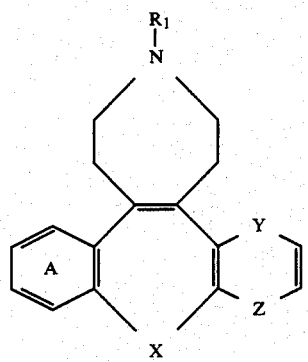

wherein
$R_1$ represents hydrogen, lower alkyl, cycloalkyl-lower alkyl of not more than 10 carbon atoms, lower alkenyl, lower alkynyl, (di-lower alkylamino)-lower alkyl, free, etherified or esterified hydroxy-lower alkyl, etherified mercapto-lower alkyl, substituted or unsubstituted phenyl-lower alkyl, or lower alkanoyl,
the ring A is unsubstituted or substituted by halogen with an atomic number up to 35, lower alkyl, hydroxyl, lower alkoxy, alkanoyloxy, lower alkylthio, trifluoromethyl or cyano,
X represents epoxy, epithio, methylene, a direct bond or a divalent radical of the partial formula

in which $R_3$ represents hydrogen or lower alkyl, and one of the radicals Y and Z represents vinylene or epithio and
the other represents a direct bond.

The subject matter of the invention also comprises the acid addition salts of the compounds of the formula I, in particular the pharmaceutically acceptable acid addition salts.

In the above definition of the formula I and throughout this specification, the term "lower" used to qualify organic groups and radicals denotes that these contain not more than 8, preferably not more than 4, carbon atoms.

Lower alkyl radicals represented by $R_1$ preferably contain 1 to 6 carbon atoms. These lower alkyl radicals, which can be straight-chain or branched, are for example methyl, ethyl, propyl, isopropyl, butyl, isobutyl or tert. butyl.

A cycloalkyl-lower alkyl radical represented by $R_1$ contains preferably 4 to 8 carbon atoms and is, for example, cyclopropylmethyl cyclobutylmethyl and, in particular, cyclopentylmethyl, cyclohexylmethyl, and also, for example, cyclopropylethyl, cyclobutylethyl, cyclopentylethyl, cyclohexylethyl.

A lower alkenyl radical $R_1$ contains preferably 3 to 4 and, in particular, 3 carbon atoms, and is for example allyl or 2-methylallyl.

A lower alkynyl radical $R_1$ is in particular propargyl.

In a (di-lower alkylamino)-lower alkyl radical $R_1$, the nitrogen atom is separated from the ring nitrogen atom by at least 2 carbon atoms. This radical contains preferably not more than 10, in particular from 4 to 6, carbon atoms. The lower alkyl moieties in this substituent are preferably straight-chain. The entire radical is for example diethylaminobutyl, diethylaminopropyl or diethylaminoethyl, dimethylaminobutyl, dimethylaminoethyl and, in particular, dimethylaminopropyl.

The hydroxyl group in a hydroxy-lower alkyl radical $R_1$ is separated from the ring nitrogen atom by at least 2 carbon atoms. This radical contains 2 to 8, preferably 2 to 6, carbon atoms, can be straight-chain or branched, and is for example 1-methyl-2-hydroxyethyl, 2-hydroxypropyl, 1- or 2-methyl-2-hydroxypropyl and, in particular, 2-hydroxyethyl and 3-hydroxypropyl.

The oxygen atom in a lower alkoxy-lower alkyl radical $R_1$ is separated from the ring nitrogen atom by at least 2 carbon atoms. This radical contains for example 3 to 10, preferably 3 to 6, carbon atoms, and is for example 2-methoxypropyl, 2- or 3-ethoxypropyl, 2- or 3-propoxypropyl, 3-isopropoxypropyl and, in particular, 2-methoxyethyl or 2-ethoxyethyl and, preferably, 3-methoxypropyl.

The oxygen atom in an alkanoyloxy-lower alkyl radical $R_1$ is separated from the ring nitrogen atom by at least 2 carbon atoms. This radical contains for example 3 to 21, preferably 4 to 11, carbon atoms, and is for example 2-formylethyl, 2-acetyloxyethyl, 2-propionyloxyethyl, 2-acetyloxypropyl, 2-methyl-3-acetyloxypropyl or 2- or 3-propionyloxypropyl and, in particular, 3-acetyloxypropyl and 3-octanoyloxypropyl.

The sulphur atom in a lower alkylthio-lower alkyl radical $R_1$ is separated from the ring nitrogen atom by at least 2 carbon atoms. This radical contains for example 3 to 10, preferably 3 to 6, carbon atoms, and is in particular methylthioethyl or 3-methylthiopropyl.

As unsubstituted or substituted phenyl-lower alkyl in the phenyl ring, $R_1$ contains for example halogen with an atomic number up to 35, lower alkyl and lower alkoxy, methylenedioxy and trifluoromethyl, in particular chlorine, methyl and methoxy.

Lower alkanoyl is in particular acetyl, propionyl or butyryl.

The ring A can be mono- or polysubstituted. However, it is preferably monosubstituted by halogen with an atomic number up to 35, preferably by chlorine; lower alkyl of not more than 4 carbon atoms, such as ethyl, propyl, isopropyl, butyl, isobutyl, tert.-butyl and especially methyl; hydroxyl; lower alkoxy of at most 4 carbon atoms, such as ethoxy, propoxy, isopropoxy, butoxy, isobutoxy and especially methoxy; alkanoyloxy, such as formyloxy, propionyloxy and especially acetyloxy; lower alkylthio of at most 4 carbon atoms, such as ethylthio, propylthio, isopropylthio, butylthio, and especially methylthio, as well as by trifluoromethyl or cyano.

If X represents the divalent radical of the partial formula Ia

(Ia)

then $R_3$ is preferably hydrogen or lower alkyl of not more than 4 carbon atoms, such as propyl, butyl, isobutyl and, in particular, methyl or ethyl.

Preferably, Y represents a direct bond and Z represents vinylene or epithio.

Salts of compounds of the formula I are primarily acid addition salts, in particular pharmaceutically acceptable acid addition salts, for example with inorganic acids, such as hydrochloric acid, hydrobromic acid, sulphuric acid or phosphoric acid, or with organic acids, such as organic carboxylic and sulphonic acids, for example methanesulphonic acid, ethanesulphonic acid, 2-hydroxyethanesulphonic acid, acetic acid, malic acid, tartaric acid, citric acid, lactic acid, oxalic acid, succinic acid, fumaric acid, maleic acid, benzoic acid, salicylic acid, phenylacetic acid, mandelic acid or embonic acid.

The novel azatetracyclic compounds of the formula I and the acid addition salts thereof have useful pharmacological properties which act, for example, on the central nervous system. They reveal in particular a damping effect on the central nervous system and excitation-inhibiting effects (amphetamine-inhibiting effects), as can be demonstrated by means of pharmacological tests. When administered to rats in the amphetamine antagonism test in a dosage range from 0.1 to 25 mg/kg i.p. or per os [Niemegeers and Janassen, Arzneimittelforschung, Vol. 24, page 45, 1974)], they thus show excitation-inhibiting effects. Compared with the amphetamine antagonistic effect, the cataleptic effect is relatively slight. The novel azatetracyclic compounds and the pharmaceutically acceptable acid addition salts thereof can therefore be used as tranquillising, antipsychotic and excitation-inhibiting compounds for the treatment of states of agitation.

The invention relates in particular to compounds of the formula I, wherein $R_1$ represents hydrogen, lower alkyl, cycloalkyl-lower alkyl of not more than 8 carbon atoms, lower alkenyl, lower alkynyl, (di-lower alkylamino)-lower alkyl, hydroxy-lower alkyl, lower alkoxy-lower alkyl, alkanoyloxy-lower alkyl, lower alkylthio-lower alkyl, phenyl-lower alkyl, or lower alkanoyl, and the ring A is unsubstituted or monosubstituted by halogen with an atomic number up to 35, lower alkyl, hydroxy, lower alkoxy, alkanoyloxy, lower alkylthio, trifluoromethyl or cyano, X represents epoxy, epithio, methylene, a direct bond or the divalent radical of the partial formula

(Ia)

in which $R_3$ represents hydrogen or lower alkyl, and one of the radicals Y and Z represents vinylene or epithio and the other represents a direct bond, and salts, in particular acid addition salts and, most particularly, pharmaceutically acceptable acid addition salts, thereof.

The invention accordingly provides compounds of the formula I, wherein $R_1$ represents hydrogen, lower alkyl, for example methyl, ethyl, isopropyl and n-butyl, cycloalkyl-lower alkyl of 4 to 8 carbon atoms, for example cyclopentylmethyl and cyclohexylmethyl, lower alkenyl, for example allyl, lower alkynyl, for example propargyl, (di-lower alkylamino)-lower alkyl, for example dimethylaminoethyl and 3-dimethylaminopropyl, hydroxy-lower alkyl, for example 2-hydroxyethyl and 3-hydroxypropyl, lower alkoxy-lower alkyl, for example 3-methoxypropyl and 3-ethoxypropyl, alkanoyloxy-lower alkyl, for example 3-acetyloxypropyl and 3-octanoyloxypropyl, lower alkylthio-lower alkyl, for example 2-methylthioethyl and 2-ethylthioethyl, 3-methylthiopropyl and 2-ethylthiopropyl, phenyl-lower alkyl, for example benzyl and phenylethyl or lower alkanoyl for example acetyl as propionyl, the ring A is unsubstituted or substituted by halogen with an atomic number up to 35, lower alkyl, hydroxy, lower alkoxy, alkanoyloxy, lower alkylthio, trifluoromethyl or cyano, X represents epoxy, epithio, methylene, a direct bond or the divalent radical of the partial formula Ia

(Ia)

in which $R_3$ represents hydrogen or lower alkyl of not more than 4 carbon atoms, preferably methyl or ethyl, and one of the radicals Y and Z represents vinylene or epithio and the other represents a direct bond, and salts, in particular acid addition salts, most particularly pharmaceutically acceptable acid addition salts, thereof.

The invention provides in particular compounds of the formula I, wherein $R_1$ represents hydrogen, lower alkyl, for example methyl or ethyl; cycloalkyl-lower alkyl of 4 to 8 carbon atoms, for example cyclopentylmethyl and cyclohexylmethyl; lower alkenyl, for example allyl; lower alkynyl, for example propargyl; (di-lower alkylamino)-lower alkyl, for example dimethylaminoethyl and 3-dimethylaminopropyl; hydroxy-lower alkyl, for example 2-hydroxyethyl and 3-hydroxypropyl; lower alkoxy-lower alkyl, for example 3-methoxypropyl; alkanoyloxy-lower alkyl, for example acetoxypropyl and octanoyloxypropyl; lower alkylthio-lower alkyl, for example 2-methylthioethyl and 3-methylthiopropyl; phenyl-lower alkyl, for example benzyl and phenylethyl; or lower alkanoyl, for example acetyl or propionyl; the ring A is unsubstituted or substituted by chlorine, bromine, methyl, hydroxy, methoxy, methylthio or cyano, X represents epoxy, epithio, methylene or the divalent radical of the partial formula Ia

(Ia)

wherein $R_3$ represents hydrogen, methyl or ethyl, and Y represents a direct bond and Z represents vinylene or epithio, and salts, in particular acid addition salts, most particularly pharmaceutically acceptable acid addition salts, thereof.

The preferred compounds are those of the formula I wherein $R_1$ represents lower alkyl, for example methyl or ethyl or cyclopentylmethyl, and the ring A is unsubstituted or substituted by chlorine, methyl, methoxy or cyano, preferably in the 7-position in the ring A of compounds in which Z represents vinylene, X represents epoxy, epithio, or methylene, or the divalent radical of the partial formula Ia

(Ia)

wherein $R_3$ represents hydrogen, methyl or ethyl and Y represents a direct bond and Z represents vinylene or epithio, such as 3-methyl-2,3,4,5-tetrahydro-1H-dibenzo[2,3:6,7]thiepino[4,5-d]azepine, 3-methyl-2,3,4,5-tetrahydro-1H-dibenzo[2,3:6,7]oxepino[4,5-d]azepine, 3-methyl-7-cyano-2,3,4,5-tetrahydro-1H-dibenzo[2,3:6,7]-thiepino[4,5-d]azepine, 3-methyl-1,2,3,4,5,10-hexahydro-dibenzo[3,4,:6,7]cyclohepta[1,2-d]azepine or 2,3,4,5-tetrahydro-1H-dibenzo[2,3:6,7]thiepino[4,5-d]azepin-propanol, and salts thereof, in particular acid addition salts, most particularly pharmaceutically acceptable acid addition salts, thereof.

The compounds of the formula I are obtained in a manner which is known per se. Thus they are obtained, for example, by reacting a reactive diester of a diethanol of the formula

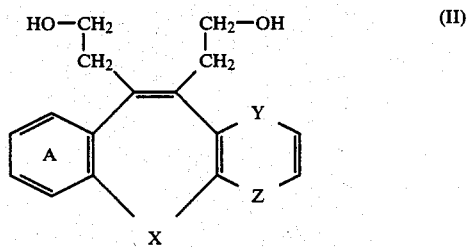
(II)

with a compound of the formula

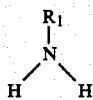
(III)

As reactive diesters of a diethanol of the formula II it is possible to use esters of strong inorganic acids, for example esters of bis-hydrochloric acid, bis-hydroiodic acid or, in particular, esters of bis-hydrobromic acid or hydrobromic-hydrochloric acid. Furthermore, corresponding diesters of strong organic acids, for example of sulphonic acids, such as methanesulphonic acid, benzenesulphonic acid, p-chloro- or p-bromobenzenesulphonic acid or p-toluenesulphonic acid, can also be used. These diesters of compounds of the formula II are preferably reacted in a suitable inert solvent at a reaction temperature between 20° and 130° C. Examples of suitable inert solvents are: hydrocarbons, such as benzene or toluene, halogenated hydrocarbons, such as chloroform, lower alcohols, such as ethanol and, in particular, methanol, ethereal liquids, such as ether or dioxan, as well as lower alkanones, for example acetone, methyl ethyl ketone or diethyl ketone, or mixtures of such solvents, for example benzenemethanol.

During the reaction of one molar equivalent of a diester of a diethanol of the formula II with one molar equivalent of a free base of the formula III two molar equivalents of acid, which are preferably bonded to an acid acceptor, are split off. Examples of suitable acid acceptors are alkali carbonates, such as potassium carbonate, or alkali hydroxides, for example sodium hydroxide or potassium hydroxide, or excess base of the formula III, and also tertiary organic bases, such as pyridine and especially triethylamine or N-ethyl-diisopropylamine.

The direct starting materials, i.e. the reactive diesters of the formula II, can be obtained from the corresponding diethanols by esterification or replacement of the hydroxyl groups by halogen by conventional methods. The diethanols can be obtained in turn from the corresponding dimethyl acetates by reduction with lithium aluminium hydride. The methyl diacetates can be obtained from the corresponding diacetonitriles with methanol and 2 molar equivalents of water by introducing hydrogen chloride. The diacetonitriles can be obtained in turn from the corresponding bis-(bromoethyl) compounds with sodium cyanide.

A further process gives compounds of the formula I in which $R_1$ represents the group $R_1'$ which has the same meaning as $R_1$, with the exception of esterified hydroxy-lower alkyl, by reducing a compound of the formula

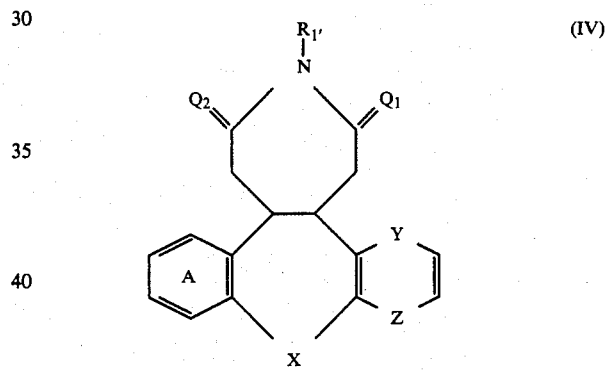
(IV)

wherein at least one the symbols $Q_1$ and $Q_2$ represents an oxygen atom and the other can represent 2 hydrogen atoms.

The reduction is advantageously carried out with a complex hydride, such as lithium aluminium hydride or diborane or aluminium hydride. The preferred solvent is an ethereal liquid, such as diethyl ether, tetrahydrofuran, dioxan, ethylene glycol dimethyl ether or diethylene glycol dimethyl ether. The reaction temperature is preferably between approx. 0° and 100° C., or the boiling temperature of the reaction medium employed. The diborane can either be prepared separately and introduced or formed in situ from sodium boronhydride and boron trifluoride etherate. It is possible to use additionally an activator, such as aluminium chloride, for the reaction with lithium aluminium hydride.

The N-substituted lactam and imide compounds as starting materials of the formula IV can be prepared by substitution of the corresponding compounds of the formula IV which are not N-substituted. This N-substitution can be effected by known methods, for example with a reactive ester of a corresponding hydroxy compound of the formula $R_1'$—OH, in which $R_1'$ is as defined above with the exception of hydrogen.

The imides of the formula IV which are not N-substituted can be obtained from the compounds of the formula VII, namely by formation of the azepine ring with hydrogen bromide and subsequent treatment with water and dimethyl formamide. The corresponding lactams can be obtained from these imides by partial reduction with a complex anhydride in an ethereal solvent, such as diethyl ether or tetrahydrofuran.

Subsequent to the reactions according to the invention, a number of conversions can be effected to convert the compounds of the formula I into other compounds of the formula I.

If desired, a compound of the formula I, whose radical $R_1$ represents hydrogen, can be converted into a product whose radical $R_1$ has one of the other meanings.

Thus, for example, a N-substitution can be effected either with a reactive ester of a corresponding alcohol of the formula $R_1^{IV}$—OH, in which $R_1^{IV}$ has the same meaning as $R_1$ in formula I with the exception of hydrogen, or by a reaction with corresponding aldehydes or ketones under reducing conditions.

The reaction of compounds of the formula I, in which $R_1$ represents hydrogen, with a reactive ester of a hydroxy compound of the formula $R^{IV}$—OH, is preferably carried out in a solvent at a reaction temperature between 20° and 130° C., in particular at the boiling temperature of the solvent.

Examples of suitable reactive esters are: halides, such as chlorides or bromides, also sulphonates, such as methyl or ethyl ortho- or para-toluenesulphonate, or sulphates, for example dimethyl or diethyl sulphate. Suitable acid acceptors are alkali metal carbonates, for example potassium carbonate, or alkali hydroxides, for example sodium hydroxide, or tertiary organic bases, for example pyridine or N-ethyl diisopropylamine. Suitable solvents are those which are inert under the reaction conditions, for example hydrocarbons, such as benzene or toluene, and alkanols, for example methanol, or ethanol, or alkanones, such as acetone or methyl ethyl ketone.

Aldehydes and ketones which correspond to the alcohols of the formula $R_1^{IV}$—OH are for example lower aliphatic aldehydes or ketones, lower free, esterified or etherified hydroxyoxoalkanes or esterified oxoalkanecarboxylic acids. The reaction product obtained during the reaction of these aldehydes or ketones with the compounds of the formula I can be reduced in the same process step or subsequently.

The aldehydes, for example formaldehyde or acetaldehyde, or the ketones, for example acetone, are heated for example with the compounds of the formula I in an inert solvent to approx. 30°–100° C., and simultaneously or subsequently the reaction mixture is hydrogenated with hydrogen in the presence of a catalyst. Examples of suitable solvents are alkanols, such as methanol or ethanol, and suitable catalysts are noble metal catalysts, such as palladium on charcoal or alloy skeleton catalysts, such as Raney nickel.

Instead of using hydrogen in the presence of a catalyst, it is also possible to use other reducing agents, for example formic acid, for the reductive alkylation. In this modification of the process, the compounds of the formula I are heated with formic acid and the types of aldehydes or ketones referred to above, in particular formaldehyde, preferably without a solvent.

This N-alkylation can also be performed by first acylating the process product in which the radical $R_1$ represents hydrogen and then acylating the carbonyl group. This reduction is advantageously carried out with a complex hydride, such as lithium aluminium hydride or diborane. The preferred solvent is an ethereal liquid, such as diethyl ether, tetrahydrofuran, dioxan, ethylene glycol dimethyl ether or diethylene glycol dimethyl ether. The reaction temperature is preferably between approx. 0° and 100° C. or the boiling temperature of the reaction medium employed. The diborane can be prepared separately and introduced or formed in situ from sodium boronhydride and boron trifluoride etherate.

If desired, a compound of the formula I, in which the radical $R_1$ represents a hydroxy-lower alkyl group, can be acylated to give a compound in which the radical $R_1$ represents an esterified hydroxy-lower alkyl group.

The acylation can be carried out for example with a carboxylic acid anhydride or with a corresponding carbonyl halide at a reaction temperature between approx. 20° and 100° C. Since the condensation takes place accompanied by elimination of acid, it is advantageous to add an acid acceptor, for example a tertiary organic base, such as pyridine, to the reaction mixture. Excess tertiary organic base can also be used as solvent. It is also possible to use a hydrocarbon, for example benzene or toluene, or a halogenated hydrocarbon, for example chloroform, as solvent.

In addition, a compound of the formula I, in which the radical $R_1$ represents a phenyl-lower alkyl group, can be subjected to hydrogenolysis to give a process product in which the radical $R_1$ represents hydrogen.

The hydrogenolysis can be carried out using conventional hydrogenation catalysts, for example noble metal catalysts, such as palladium on carbon or platinum oxide, of rhodium catalysts, such as rhodium on carbon or on aluminium oxide, or of alloy skeleton catalysts, such as Raney nickel, in an inert organic solvent, such as methanol, ethanol or dioxan, at room temperature and normal pressure or at moderately elevated temperature to approx. 100° C. and/or elevated pressure up to approx. 100 bar.

Furthermore, a compound of the formula I, in which X represents a divalent radical of the partial formula

(Ia)

in which $R_3$ represents hydrogen, can optionally be converted into another process product in which the radical $R_3$ represents lower alkyl.

This conversion is advantageously carried out in such a manner that the above process product is reacted in the presence of solvents and basic condensation agents with a reactive lower alkyl ester.

Examples of reactive esters which can be used are: halides, such as chlorides or bromides, and sulphonates, such as methyl or ethyl ortho- or para-toluenesulphonate, or sulphates, for example dimethyl or diethyl sulphate. Suitable basic condensation agents are alkali metal alkanolates, such as potassium tert.-butylate, or corresponding amides, such as sodium amide, or metal hydrides, such as sodium or lithium hydride. Suitable solvents are those which are inert under the reaction conditions, for example hydrocarbons, such as benzene or toluene, and ethereal liquids, for example tetrahydrofuran, dioxan, ethylene glycol dimethyl ether, or amides, such as phosphoric hexamethyl triamide or dimethyl formamide.

This conversion can, however, be carried out in such a manner that the process product is first acylated and the carbonyl group then reduced.

This reduction is preferably carried out with a hydride. The preferred hydride is diborane in an ethereal reaction medium, such as tetrahydrofuran, dioxan, ethylene glycol dimethyl ether or diethylene glycol dimethyl ether. The reaction temperature is preferably between −20° and +80° C., preferably between 0° C. and room temperature. The diborane is formed for example from boron trifluoride etherate and sodium borohydride either separately, for example in the solvent used for the reduction, and used as a solution, or, for example, formed in diethylene glycol dimethyl ether and introduced into the reaction mixture in gaseous form, or else formed in situ.

Depending on the process conditions and the starting materials, the final products are obtained in the free form or in the form of their salts, which can be converted into each other or into other salts in conventional manner. Thus free compounds of the formula I are formed from resultant acid addition salts, for example by treatment with bases or ion exchangers, whilst free bases of the formula I are converted into acid addition salts, for example by reaction with organic or inorganic acids, in particular those which are suitable for the formation of pharmacologically acceptable salts, such as those mentioned above.

Salts of the novel compounds can also be used for purification purposes, for example by converting the free compounds into their salts, isolating these and optionally purifying and converting them again into the free compounds. Because of the close relationship between the novel compounds in the free form and in the form of their salts, what is stated in this specification in respect of the free compounds applies by analogy also to the corresponding salts.

The invention also relates to those modifications of the process in which a compound obtainable in any stage as intermediate is used as starting material and the missing process steps are carried out, or the process is discontinued at any stage, or in which a starting material is formed under the reaction conditions or in which a reaction component is optionally in the form of a derivative, for example in the form of a salt.

It is advantageous to use for carrying out the reactions of the present invention those starting materials which result in the groups of end products particularly referred to at the outset and especially in the end products described or singled out for special mention.

The novel compounds can be used for example in the form of pharmaceutical compositions which contain an effective amount of the active substance, if appropriate together with inorganic or organic, solid or liquid pharmaceutically useful carriers suitable for enteral, for example oral, or parenteral administration. Tablets or gelatin capsules are therefore used which contain the active substance together with diluents, for example lactose, dextrose, sucrose, mannitol, sorbitol, cellulose and/or glycin, and lubricants, for example silica, talc, stearic acid or salts thereof, such as magnesium or calcium stearate, and/or polyethylene glycol. Tablets also contain binding agents, for example magnesium aluminium silicate, starches, such as maize, corn, rice or arrow root starch, gelatins, tragacanth, methyl cellulose, sodium carboxymethyl cellulose and/or polyvinyl pyrrolidone, and, if desired, disintegrators, for example starches, agar, alginic acid or a salt thereof, such as sodium alginate, and/or effervescent mixtures, or adsorption agents, dyes, flavouring matters and sweeteners. It is also possible to use the novel pharmacologically active compounds in the form of compositions for parenteral administration or of infusion solutions. Such solutions are preferably isotonic aqueous solutions or suspensions which can be prepared before use, for example from lyophilised preparations that contain the active substance alone or together with a carrier, for example mannitol. The pharmaceutical compositions can be sterilised and/or contain adjuvants, for example preservatives, stabilisers, wetting agents and/or emulsifiers, solubility promoters, salts for regulating the osmotic pressure and/or buffers. The pharmaceutical compositions which, if desired, can contain further pharmacologically useful substances, are manufactured in known manner, for example using conventional mixing, granulating, confectioning, dissolving or lyophilising methods, and they contain from about 0.1% to 100%, especially from about 1% to about 50%, of lyophilisates up to 100% of the active substance.

The dosage depends on the mode of application, species, age, and on the individual condition. The daily doses of the free bases or of pharmaceutically acceptable salts thereof are between approx. 0.1 mg/kg and approx. 10 mg/kg for warm-blooded animals in general, and between approx. 0.01 g and approx. 0.5 g for warmblooded animals having a weight of approx. 70 kg.

The invention is illustrated by the following Examples.

EXAMPLE 1

To a solution of 21.8 g (0.05 mole) of 10,11-bis-[2-(methylsulphonyloxy)-ethyl]-5H-dibenzo[a,d]cycloheptene in 200 ml of absolute ethanol are added 35 ml (2.6 g, 0.06 mole) of a 7.4% ethanolic ethylamine solution and 15.5 g (0.125 mole) of diisopropyl ethylamine. The reaction mixture is refluxed for 18 hours, then concentrated in a water jet vacuum. The residue is dissolved in 300 ml of methylene chloride and the solution is washed in succession with 100 ml of 2N sodium hydroxide solution and 100 ml of water. The methylene chloride solution is concentrated in a water jet vacuum to approx. 50 ml and treated with 15 ml of 4N ethereal hydrogen chloride solution, whereupon the 3-ethyl-1,2,3,4,5,10-hexahydro-dibenzo[3,4:6,7]cyclohepta[1,2-d]azepine hydrochloride with a melting point of 296°–299° C. crystallises out. Melting point of the methanesulphonate: 220°–221° C.

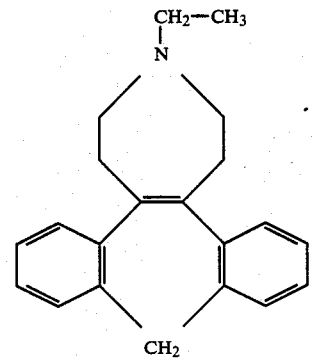

The starting material can be prepared in the following manner in accordance with the particulars of Example 5: dimethyl 5H-dibenzo[a,d]cycloheptane-10,11-diacetate, m.p. 104°–106° C. (from hexane), starting from 27 g (0.1 mole) of 5H-dibenzo[a,d]cycloheptene-10,11-diacetonitrile, 400 ml of methanol, 3.8 ml of water and dry hydrogen chloride; 5H-dibenzo[a,d]cycloheptane-10,11-diethanol, m.p. 154°–156° C. (from acetone), starting from 33.6 g (0.1 mole) of dimethyl 5H-dibenzo[a,d]cycloheptane-10,11-diacetate and 7.6 g (0.2 mole) of lithium aluminium hydride in 1 liter of abs. diethyl ether.

To a solution of 28 g (0.10 mole) of 5H-dibenzo[a,d]cycloheptene-10,11-diethanol in 120 ml of pyridine are added dropwise 16.8 ml (25.2 g, 0.22 mole) of methanesulphonyl chloride at room temperature. The reaction mixture is thereafter stirred for 30 minutes at 0° C. and then for 1 hour at 15°–25° C., then together with 600 ml of methylene chloride is extracted in a separating funnel in succession with 400 ml of 5N hydrochloric acid and 400 ml of ice-water. The methylene chloride solution is separated, dried over magnesium sulphate and concentrated in a water jet vacuum, to give as residue 10,11-bis-[2-(methylsulphonyloxy)-ethyl]-5H-dibenzo[a,d]cycloheptane in the form of a colourless oil.

The following compounds can be prepared in analogous manner:

3-methyl-1,2,3,4,5,10-hexahydro-dibenzo[3,4:6,7]cyclohepta[1,2-d]azepine methanesulphonate, m.p. 189°–191° C., starting from 21.8 g (0.05 mole) of 10,11-bis-[2-(methylsulphonyloxy)-ethyl]-5H-dibenzo[a,d]cycloheptane, 30 ml (1.9 g, 0.06 mole) of a 6.3% ethanolic methylamine solution and 15.5 g (0.125 mole) of diisopropyl ethylamine.

3-benzyl-1,2,3,4,5,10-hexahydro-dibenzo[3,4:6,7]cyclohepta[1,2-d]azepine hydrochloride, m.p. 265°–270° C., starting from 21.8 g (0.05 mole) of 10,11-bis-[2-(methylsulphonyloxy)-ethyl]-5H-dibenzo[a,d]cycloheptene, 6.2 g (0.06 mole) of benzylamine and 15,5 g (0.125 mole) of diisopropyl ethylamine.

EXAMPLE 2

A suspension of 19.4 g (0.05 mole) of 3-benzyl-1,2,3,4,5,10-hexahydro-dibenzo[3,4:6,7]cyclohepta[1,2-d]azepine hydrochloride and 2 g of 5% palladium on charcoal catalyst in 900 ml of methanol is hydrogenated at normal pressure and 40°–50° C. until 770 ml of hydrogen have been taken up. The catalyst is then removed by suction filtration and the filtrate is concentrated in a water jet vacuum.

The residual crude 1,2,3,4,5,10-hexahydro-dibenzo[3,4:6,7]cyclohepta[1,2-d]azepine hydrochloride is recrystallised from ethanol. Melting point: 295°–300° C.

The base is set free by suspending the hydrochloride in 250 mol of methylene chloride and extraction with 100 ml of conc. ammonia solution. The methylene chloride solution is separated and concentrated until the onset of crystallisation. Then hexane is added, whereupon the 1,2,3,4,5,10-hexahydro-dibenzo[3,4:6,7]cyclohepta[1,2-d]azepine with a melting point of 190°–191° C. crystallises out.

For conversion into the methanesulphonate, the free base is dissolved in methylene chloride and after addition of the theoretical amount of methanesulphonic acid the 1,2,3,4,5,10-hexahydro-dibenzo[3,4:6,7]cyclohepta[1,2-d]azepine methanesulphonate is precipitated with ether. Melting point: 269°–271° C.

EXAMPLE 3

To a solution of 43.6 g (0.1 mole) of 10,11-bis-[2-(methylsulphonyloxy)-ethyl]-5H-dibenzo[a,d]cycloheptane in 400 ml of absolute ethanol are added 11.9 g (0.12 mole) of (aminomethyl)-cyclopentane and 32.3 g (0.25 mole) of diisopropyl ethylamine. The reaction mixture is then concentrated in a water jet vacuum, the residue dissolved in 150 ml of methylene chloride and 500 ml of pentane, and the solution washed in succession with 200 ml of 2N sodium hydroxide solution and 200 ml of water. The organic phase is subsequently treated with 200 ml of 2N hydrochloric acid and the hydrochloride precipitates in crystals. The crystals are collected with suction and the base is set free by suspending the hydrochloride in 300 ml of methylene chloride and extraction with 100 ml of conc. ammonia solution.

The methylene chloride solution is separated and concentrated until the onset of crystallisation. After the addition of hexane, the 3-(cyclopentyl-methyl)-1,2,3,4,5,10-hexahydro-dibenzo[3,4:6,7]cyclohepta[1,2-d]azepine with a melting point of 141°–142° C. crystallises out. For conversion into the methanesulphonate, the base is dissolved in methylene chloride, the solution is acidified with the theoretical amount of methanesulphonic acid, and the 3-(cyclopentylmethyl)-1,2,3,4,5,10-hexahydro-dibenzo[3,4:6,7]cyclohepta[1,2-d]azepine methanesulphonate is precipitated with ether. Melting point: 248°–249° C.

EXAMPLE 4

With ice cooling, 26.1 g (0.1 mole) of 1,2,3,4,5,10-hexahydro-dibenzo[3,4:6,7]cyclohepta[1,2-d]azepine (prepared in accordance with Example 2) are treated with 92 g (2 moles) of formic acid and 20 g (0.2 mole) of 30% formaldehyde and the reaction mixture is stirred for 1 hour at 95°–100° C. The mixture is then poured onto ice-water and made alkaline with 10N sodium hydroxide solution. The precipitated base is taken up in methylene chloride and the methylene chloride solution is concentrated until the onset of crystallisation. Then hexane is added, whereupon the 3-methyl-1,2,3,4,5,10-hexahydro-dibenzo[3,4:6,7]cyclohepta[1,2-d]azepine with a melting point of 144°–146° C. crystallises out. For conversion into the methanesulphonate, the base is dissolved in methylene chloride, the solution is treated with the theoretical amount of methanesulphonic acid, and the 3-methyl-1,2,3,4,5,10-hexahydro dibenzo[3,4:6,7]cyclohepta[1,2-d]azepine methanesulphonate is precipitated with ether. Melting point: 189°–191° C.

EXAMPLE 5

To a solution of 4.56 g (0.01 mole) of 10,11-bis-[2-(methylsulphonyloxy)-ethyl]-dibenzo[b,f]thiepine in 50 ml of absolute ethanol are added 1.3 g (0.012 mole) of benzylamine and 3.25 g (0.0125 mole) of diisopropyl ethylamine and the reaction mixture is refluxed for 18 hours. After cooling with an ice bath, crystals precipitate and are collected with suction and washed with a small amount of isopropanol and pentane. The filter cake consists of 3-benzyl-2,3,4,5-tetrahydro-1H-dibenzo[2,3:6,7]thiepino[4,5-d]-azepine with a melting point of 149°–150° C.

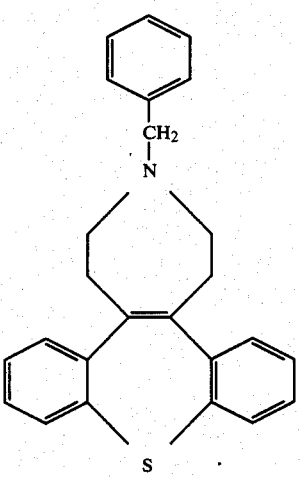

For conversion into the hydrochloride, 3 g of the base are dissolved in acetone and 2.2 ml of a 4N hydrogen chloride solution in ether are added to this solution. Then ether is added until the solution becomes slightly turbid and the 3-benzyl-2,3,4,5-tetra-1H-dibenzo[2,3:6,7]thiepino[4,5-d]-azepine hydrochloride crystallises out. Melting point: 241°–242° C.

The starting material can be prepared as follows: With stirring, 58 g (0.2 mole) of dibenzo[b,f]thiepine-10,11-diacetonitrile are suspended in 800 ml of methanol and 7.5 ml of water and the suspension is cooled in an ice bath to 0°–5° C. Then dry hydrogen chloride is introduced in the course of 1 hour and a clear solution forms. (During this introduction the temperature should be kept at 5°–20° C.). The reaction mixture is further stirred for 1 hour at room temperature and then for 4 hours at reflux and thereafter completely evaporated to dryness by rotary evaporation. The residue is dissolved in ether and the ethereal solution is washed with water and 2N sodium carbonate solution, dried over sodium sulphate, and completely evaporated to dryness. The oily residue is dissolved in methanol and the solution is cooled to 0° C., whereupon methyl dibenzo[b,f]thiepine-10,11-diacetate crystallises out. The product is collected with suction and dried at 50° C. under reduced pressure. Melting point: 84°–86° C.

With stirring and exclusion of moisture, a solution of 35.4 g (0.1 mole) of dimethyl dibenzo[b,f]thiepine-10,11-diacetate in 1 liter of absolute diethyl ether is added dropwise, in a nitrogen atmosphere and in the course of 1 hour, to a suspension or 7.6 g (0.2 mole) of lithium aluminium hydride in 400 ml of absolute diethyl ether. The reaction mixture is subsequently refluxed for 16 hours, then cooled to 0° C. and diluted with 130 ml of water (dropwise addition). The organic phase is separated, washed with water, dried over sodium sulphate, and concentrated to a small volume, whereupon dibenzo[b,f]thiepine-10,11-diethanol with a melting point of 131°–133° C. crystallises out.

15 g (0.05 mole) of dibenzo[b,f]thiepine-10,11-diethanol are dissolved at room temperature in 60 ml of pyridine and the solution is treated dropwise in an ice-sodium chloride bath, at a reaction temperature of −5° C., with 8.4 ml (12.6 g, 0.11 mole) of methanesulphonyl chloride. The reaction mixture is subsequently stirred for 30 minutes at 0° C. and then for 1 hour at 15°–25° C. Together with 500 ml of methylene chloride the reaction mixture is then extracted in a separating funnel in succession with 400 ml of 2N hydrochloric acid and 400 ml of water. The methylene chloride solution is separated, dried over magnesium sulphate, and concentrated in a water jet vacuum to give as residue 10,11-bis-[2-(methylsulphonyloxy)-ethyl]-dibenzo[b,f]thiepine with a melting point of 107°–108° C.

EXAMPLE 6

In accordance with the procedure described in Example 5, the following compounds can be prepared using the corresponding starting materials:

(A) 3-(2-phenylethyl)-2,3,4,5-tetrahydro-1H-dibenzo[2,3:6,7]thiepino[4,5-d]azepine with a melting point of 96°–99° C. (from acetonitrile); melting point of the methanesulphonate 161°–164° C. (from abs. ethanol); starting from 22.7 g (0.05 mole) of 10,11-bis-[2-(methylsulphonyloxy)-ethyl-dibenzo[b,f]thiepine, 7.3 g (0.06 mole) of 2-phenylethylamine and 16.25 g (0.125 mole) of diisopropyl ethylamine in abs. ethanol;

(B) 7-methoxy-3-methyl-2,3,4,5-tetrahydro-1H-dibenzo[2,3:6,7]thiepino[4,5-d]azepine, melting point 108°–112° C. (from acetone); melting point of the hydrochloride 220°–224° C. (from abs. ethanol); starting from 24.2 g (0.05 mole) of 10,11-bis-[2-(methylsulphonyloxy)-ethyl]-2-methoxy-dibenzo[b,f]thiepine, 1.85 g of methylamine (0.06 mole) and 16.25 g (0.125 mole) of diisopropyl ethylamine in abs. ethanol;

(C) 7-methylthio-3-(cyclopentylmethyl)-2,3,4,5-tetrahydro-1H-dibenzo[2,3:6,7]thiepino[4,5-d]azepine, crude product; melting point of the methanesulphonate 206°–209° C. (from abs. ethanol); starting from 25 g (0.05 mole) of 10,11-bis-[2-(methylsulphonyloxy)-ethyl]-2-methylthio-dibenzo[b,f]thiepine, 6 g (0.06 mole) of (aminomethyl)-cyclopentane and 16.25 g (0.125 mole) of diisopropyl ethylamine in abs. ethanol;

(D) 3,7-dimethyl-2,3,4,5-tetrahydro-1H-dibenzo[2,3:6,7]thiepino[4,5-d]azepine, crude product; melting point of the hydrochloride 265°–268° C. (from abs. ethanol); starting from 23.4 g (0.05 mole) of 10,11-bis-[2-(methylsulphonyloxy)-ethyl]-2-methyl-dibenzo[b,f]thiepine, 1.85 g (0.06 mole) of methylamine and 16.25 g (0.125 mole) of diisopropyl ethylamine in abs. ethanol;

(E) 7-bromo-3-methyl-2,3,4,5-tetrahydro-1H-dibenzo[2,3:6,7]thiepino[4,5-d]azepine, crude product; melting point of the hydrochloride 280° C., with decomposition (from abs. ethanol); starting from 26.7 g (0.05 mole) of 10,11-bis-[2-(methylsulphonyloxy)-ethyl]-2-bromo-dibenzo[b,f]thiepine, 1.85 g (0.6 mole) of methylamine and 16.25 g (0.125 mole) of diisopropyl ethylamine in abs. ethanol;

(F) 3-methyl-2,3,4,5-tetrahydro-1H-phenanthro[9,10-d]azepine, m.p. 142°–145° C. (from acetone), m.p. of the methanesulfonate 242°–244° C. (from ethanol); starting from 21.1 g (0.05 mole) of 9,10-bis-[2-(methylsulphonyloxy)-ethyl]-phenanthrene, 1.85 g (0.06 mole) of methylamine and 16.25 g (0.125 mole) of diisopropylethylamine in abs. ethanol;

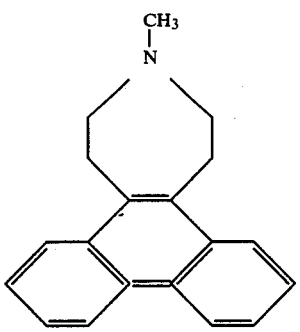

(G) 3-methyl-2,3,4,5-tetrahydro-1H-thieno[2',3':1,2-]naphtho[4,5-d]azepine, crude of product; m.p. of the hydrochloride 273°-280° C. with decomposition (from methanol); starting from 21.4 g (0.05 mole) of 4,5-bis-[2-(methylsulphonyloxy)-ethyl]naphthol[1,2-b]thiophene, 1.85 g (0.06 mole) of methylamine and 16.25 g (0.125 mole) of diisopropylethylamine;

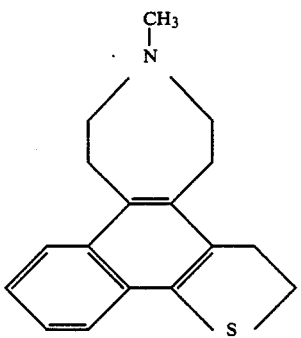

(H) 3-methyl-2,3,4,5-tetrahydro-1H-dibenz[2,3:6,-7]oxepino[4,5-d]azepine, m.p. 147°-149° C. (from acetonitrile); m.p. of the hydrochloride 282°-285° C. (from abs. ethanol); starting from 21.9 g (0.05 mole) of 10,11-bis-[2-(methylsulphonyloxy)-ethyl]dibenz[b,f]oxepine, 1.85 g (0.06 mole) of methylamine and 16.25 g (0.125 mole) of diisopropyl ethylamine;

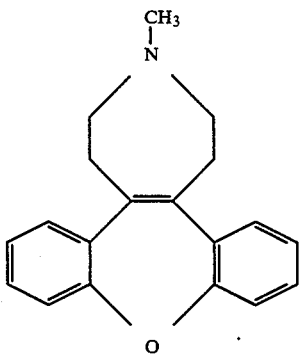

(I) 3-isopropyl-2,3,4,5-tetrahydro-1H-dibenz[2,3:6,-7]oxepino[4,5-d]azepine, m.p. 125°-128° C. (from acetonitrile); m.p. of the maleate 175°-177° C. (from acetone); starting from 21.9 g (0.05 mole) of 10,11-bis-[2-(methylsulphonyloxy)-ethyl]dibenz[b,f]oxepine, 3.5 g (0.06 mole) of isopropylamine and 16.25 g (0.125 mole) of diisopropyl ethylamine;

(K) 3-methyl-10-ethyl-1,2,3,4,5,10-hexahydro-dibenz[b,f]azepino[4,5-d]azepine, m.p. 99°-100° C. (from toluene); m.p. of the oxalate 180°-183° C. (from abs. ethanol); starting from 23.3 g (0.05 mole) of 10,11-bis-[2-(methylsulphonyloxy)-ethyl]-5-ethyl-5H-dibenz[b,f]azepine, 1.85 g (0.006 mole) of methylamine and 16.25 g (0.125 mole) of diisopropyl ethylamine;

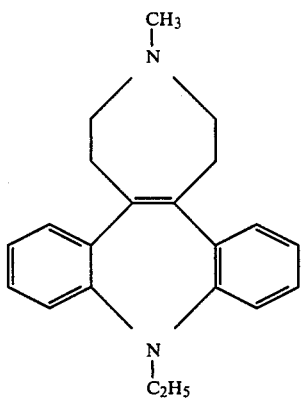

(L) 3-allyl-10-ethyl-1,2,3,4,5,10-hexahydro-dibenz[b,-f]azepino[4,5-d]azepine, m.p. 100°-101° C. (from hexane); m.p. of the hydrochloride 245°-248° C. (from abs. ethanol/acetone); starting from 23.3 g (0.05 mole) of 10,11-bis-[2-(methylsulphonyloxy)-ethyl]-5-ethyl-5H-dibenz[b,f]azepine, 3.4 g (0.06 mole) of allylamine and 16.25 g (0.125 mole) of diisopropyl ethylamine;

(M) 3-methyl-1,2,3,4,5,10-hexahydro-dibenz[b,-f]azepino[4,5-d]azepine, m.p. 121°-124° C. (from methanol); m.p. of the methanesulphonate 263°-266° C. (from abs. ethanol/acetone); and starting from 21.9 g (0.05 mole) of 10,11-bis-[2-(methylsulphonyloxy)-ethyl]-5H-dibenz[b,f]azepine, 1.85 g (0.06 mole) of methylamine and 16.25 g (0.125 mole) of diisopropyl ethylamine;

(N) 3-(cyclopentylmethyl)-1,2,3,4,5,10-hexahydro-dibenz[b,f]azepino[4,5-d]azepine, m.p. 72°-75° C. (from pentane); m.p. of the methanesulphonate 271°-274° C. (from methanol); starting from 21.9 g (0.05 mole) of 10,11-bis-[2-(methylsulphonyloxy)-ethyl]-5H-dibenz[b,-f]azepine, 6.0 g (0.06 mole) of (aminomethyl)-cyclopentane and 16.25 g (0.125 mole) of diisopropyl ethylamine.

The starting materials can be prepared as follows: for
(B) 2-methoxy-dibenzo[b,f]thiepine-10,11-diacetonitrile, m.p. 198°-200° C. (from acetonitrile); starting from 42.3 g (0.1 mole) of 2-methoxy-10,11-bis(-bromomethyl)-dibenzo[b,f]thiepine and 11.8 g (0.24 mole) of sodium cyanide in 500 ml of a acetonitrile;

dimethyl 2-methoxy-dibenzo[b,f]thiepine-10,11-diacetate, m.p. 96°-98° C. (from toluene), starting from 31.8 g (0.1 mole) of 2-methoxy-dibenzo[b,f]thiepine-10,11-diacetonitrile, 400 ml of methanol, 3.8 ml of water and dry hydrogen chloride;

2-methoxy-dibenzo[b,f]thiepine-10,11-diethanol, m.p. 116°-119° C. (from ethyl acetate/hexane), starting from 38.5 g (0.1 mole) of dimethyl 2-methoxy-dibenzo[b,f]thiepine-10,11-diacetate and 7.6 g (0.2 mole) of lithium aluminium hydride in 1 liter of abs. diethyl ether;

10,11-bis-[2-(methylsulphonyloxy)-ethyl]-2-methoxy-dibenzo[b,f]thiepine, crude product, starting from 32.8 g (0.1 mole) of 2-methoxy-dibenzo[b,f]thiepine-10,11-diethanol, 25.2 g (0.22 mole) of methanesulphonyl chloride in 120 ml pyridine);

for (C) 2-methylthio-dibenzo[b,f]thiepine-10,11-diacetonitrile, m.p. 204°-206° C. (from ethyl acetate); starting from 44.2 g (0.1 mole) of 2-methylthio-10,11-bis-(bromomethyl)-dibenzo[b,f]thiepine and 11.8 g (0.24 mole) of sodium cyanide is 500 ml of acetonitrile;

dimethyl 2-methylthiodibenzo[b,f]thiepine-10,11-diacetate, m.p. 85°-86° C. (from pentane), starting from 33.4 g (0.1 mole) of 2-methylthio-dibenzo[b,f]thiepine-10,11-diacetonitrile, 400 ml of methanol, 3.8 ml of water and dry hydrogen chloride; 2-methylthio-dibenzo[b,f]thiepine-10,11-diethanol, m.p. 58°-60° C. (from diethylether), starting from 40.0 g (0.1 mole) of dimethyl 2-methylthio-dibenzo[b,f]thiepine-10,11-diacetate and 7.6 g (0.2 mole) of lithium aluminium hydride to 1 liter of abs. diethyl ether;

10,11-bis-[2-(methyl-sulphonyloxy)-ethyl]-2-methylthiodibenzo[b,f]thiepine, crude product starting from 34.5 g (0.1 mole) of 2-methylthio-dibenzo[b,f]thiepine-10,11-diethyl, 25.2 g (0.22 mole) of methanesulphonyl chloride in 120 ml of pyridine;

for (D) 2-methoxy-dibenzo[b,f]thiepine-10,11-diacetonitrile, m.p. 198°-200° C. (from acetonitrile), starting from 41.0 g (0.1 mole) of 2-methyl-10,11-bis-(bromomethyl)-dibenzo[b,f]thiepine and 11.8 g (0.24 mole) of sodium cyanide in 500 ml acetonitrile;

dimethyl 2-methyl-dibenzo[b,f]thiepine-10,11-diacetate, m.p. 76°-77° C. (from methanol), starting from 30.2 g (0.1 mole) of 2-methyl-dibenzo[b,f]thiepine-10,11-diacetonitrile, 400 ml of methanol, 3.8 ml of water and dry hydrogen chloride; 2-methyl-dibenzo[b,f]thiepine-10,11-diethanol, m.p. 126°-129° C. (from acetonitrile), starting from 36.9 g (0.1 mole) of dimethyl 2-ethyl-dibenzo[b,f]thiepine-10,11-diacetate and 7.6 g (0.2 mole) of lithium aluminium hydride in 1 liter of abs. diethyl ether;

10,11-bis[2-(methylsulphonyloxy)-ethyl]2-methyl-dibenzo[b,f]thiepine, crude product, starting from 31.2 g (0.01 mole) of 2-methyl-dibenzo[b,f]thiepine-10,11-diethanol, 25.2 g (0.22 mole) of methanesulphonyl chloride in 120 ml pyridine;

for (E) 2-bromo-dibenzo[b,f]thiepine-10,11-diacetonitrile, m.p. 200°-204° C. (from acetonitrile), starting from 47.5 g (0.1 mole) of 2-bromo-10,11-bis-(bromoethyl)-dibenzo[b,f]thiepine and 11.8 g (0.24 mole) of sodium cyanide in 500 ml of a acetonitrile;

dimethyl 2-bromo-dibenzo[b,f]thiepine-10,11-diacetate, m.p. 90°-93° C. (for abs. ethanol), starting from 36.7 g (0.01 mole) of 2-bromo-dibenzo[b,f]thiepine-10,11-diacetonitrile, 400 ml of methanol, 3.8 ml of water and dry hydrogen chloride;

2-bromo-dibenzo[b,f]thiepine-10,11-diethanol, m.p. 166°-169° C. (from diethylether), starting from 43.3 g (0.1 mole) of dimethyl 2-bromo-dibenzo[b,f]thiepine-10,11-diacetate and 7.6 g (0.2 mole) of lithium aluminium hydride in 1 liter of abs. diethyl ether;

10,11-bis-[2-(methylsulphonyloxy)-ethyl]-2-bromo-dibenzo[b,f]thiepine, m.p. 94°-96° C. (from hexane ether), starting from 37.7 g (0.1 mole) of 2-bromo-dibenzo[b,f]thiepine-10,11-diethanol and 25.2 g (0.22 mole) of methanesulphonyl chloride in 120 ml of pyridine;

for (F) dimethyl phenanthrene-9,10-diacetate, m.p. 143°-145° C. (from methanol), starting from 25.6 g (0.1 mole) of phenanthrene-9,10-diacetonitrile [cf. S. Hauptmann, Chem. Ser. 93, 2604, (1960)], 400 ml of methanol, 3.8 ml of water and dry hydrogen chloride;

phenanthryl-9,10-diethanol, m.p. 175°-177° C. (from methanol), starting from 32.2 g (0.1 mole) of dimethyl phenanthrene-9,10-diacetate and 7.6 g (0.2 mole) of lithium aluminium hydride in 1 liter of abs. diethyl ether;

9,10-bis-[2-(methylsulphonyloxy)-ethyl]-phenanthrene, m.p. 157°-159° C. (from acetonitrile), starting from 26.6 g (0.1 mole) of phenanthrene-9,10-diethanol and 25.2 g (0.22 mole) of methanesulphonyl chloride in 120 mol of pyridine;

for (G) A mixture of 122 g (0.5 mole) of 4,5-dimethyl-benzo[f]thieno[2,3-b]thiepine (Case 4-3230), 980 ml of ethylene glycol and 100 g of potassium hydroxide is refluxed for 2 hours with stirring in a nitrogen atmosphere. The mixture is then cooled to 20° C., diluted with 800 ml of water and extracted with petroleum ether. The organic phase is separated, washed with water, dried over sodium sulphate and concentrated. The residue, 4,5-dimethyl-naphtho[1,2-b]thiophene, melts after recrystallisation from methanol at 88°-90° C.;

106 g (0.5 mole) of 4,5-dimethyl-naphtho[1,2-b]thiophene are dissolved in 2.5 liters of carbon tetrachloride and the solution is treated with 178 g (1 mole) of N-bromosuccinimide. With stirring and in an atmosphere of nitrogen, the mixture is heated to the boil while irradiating with a UV lamp. The mixture is kept at the boil until all the N-bromosuccinimide which lies at the bottom of the reaction vessel has become transformed into succinimide floating on the surface of the solution (time taken: approx. 20 minutes). The mixture is thereafter diluted with 400 ml of water and the crystallised 4,5-bis-(bromomethyl)-naphtho[1,2-b]thiophene (melting point: 202°-204° C.) is filtered off;

naphto[1,2-b]thiophene-4,5-diacetonitrile, m.p. 250°-251° C. (from acetone), starting from 37 g (0.1 mole) of 4,5-bis-bromomethyl-naphtho[1,2-b]thiophene and 11.8 g (0.24 mole) of sodium cyanide in 500 ml of acetonitrile;

dimethyl naphtho[1,2-b]thiophene-4,5-diacetate, m.p. 136°-138° C. (from methanol), starting from 26.2 g (0.2 mole) of naphtho[1,2-b]thiophene-4,5-diacetonitrile, 400 ml of methanol, 3.8 ml of water and dry hydrogen chloride;

naphtho[1,2-b]thiophene-4,5-diethanol, m.p. 163°-166° C. (from acetone), starting from 32.8 g (0.1 mole) of dimethyl naphtho[1,2-b]thiophene-4,5-diacetate and 7.6 g (0.2 mole) of lithium aluminium hydride in 1 liter of abs. diethyl ether;

4,5-[2-(methylsulphonyloxy)-ethyl]-naphtho[1,2-b]thiophene, m.p. 132°-135° C. (from methylene chloride), starting from 27.2 g (0.1 mole) of naphtho[1,2-b]thiophene-4,5-diethanol and 25.2 g (0.22 mole) in 120 ml of pyridine;

for (H) and (I) dibenz[b,f]oxepine-10,11-diacetonitrile, m.p. 176°-178° C. (from methanol), starting from 38 g (0.1 mole) of 10,11-bis-(bromomethyl)-dibenz[b,f]oxepine and 11.8 g (0.24 mole) of sodium cyanide in 500 ml of acetonitrile; dimethyl dibenz[b,f]oxepine-10,11-diacetate, m.p. 65°-67° C. (from pentane), starting from 27.2 g (0.1 mole) of dibenz[b,f]oxepine-10,11-diacetonitrile, 400 ml of methanol, 3.8 ml of water and dry hydrogen chloride;

dibenz[b,f]oxepine-10,11-diethanol, m.p. 138°-140° C. (from acetone), starting from 33.8 g (0.1 mole) of dimethyl dibenz[b,f]oxepine-10,11-diacetate and 7.6 g (0.2 mole) of lithium aluminium hydride in 1 liter of abs. diethyl ether;

10,11-bis-[2-(methylsulphonyloxy)-ethyl]-dibenz[b,f]oxepine, m.p. 112°-114° C. (from methylene chloride), starting from 28.2 g of dibenz[b,f]oxepine-10,11-diethanol and 25.2 g (0.22 mole) of methanesulphonyl chloride in 120 ml of pyridine;

for (K)+(L) 5-acetyl-5H-dibenz[b,f]azepine-10,11-diacetonitrile, m.p. 183°-185° C. (from benzene) starting from 42.1 g (0.1 mole) of 5-acetyl-10,11-bis-(bromomethyl)-5H-dibenz[b,f]azepine and 11.8 g (0.24 mole) of sodium cyanide in 500 ml of acetonitrile;

dimethyl 5-acetyl-5H-dibenz[b,f]azepine-10,11-diacetate, m.p. 123°-124° C. (from toluene), starting from 31.3 g (0.1 mole) of 5-acetyl-5H-dibenz[b,f]azepine-10,11-diacetonitrile;

5-ethyl-5H-dibenz[b,f]azepine-10,11-diethanol, m.p. 102°-105° C. (from ether), starting from 37.9 g (0.1 mole) of dimethyl 5-acetyl-5H-dibenz[b,f]azepine-10,11-diacetate and 7.6 g of lithium aluminium hydride in 150 ml of abs. tetrahydrofuran;

10,11-bis-[2-(methylsulphonyloxy)-ethyl]-5-ethyl-5H-dibenz[b,f]azepine, m.p. 140°-143° C. (from toluene), starting from 30.9 g (0.1 mole) of 5-ethyl-5H-dibenz[b,f]azepine-10,11-diethanol and 25.2 g (0.22 mole) of methanesulphonyl chloride in 120 ml of pyridine;

for (M)+(N) 5H-dibenz[b,f]azepine-10,11-diethanol, m.p. 180°-182° C. (from acetone), starting from 37.9 g (0.1 mole) of dimethyl 5-acetyl-5H-dibenz[b,f]azepine-10,11-diacetate;

10,11-bis-[2-(methylsulphonyloxy)-ethyl]-5H-dibenz[b,f]azepine, m.p. 140°-142° C. (from toluene), starting from 28.1 g (0.1 mole) of 5H-dibenz[b,f]azepine-10,11-diethanol and 25.2 g (0.22 mole) of methanesulphonyl chloride.

EXAMPLE 7

A mixture of 16.2 g (0.05 mole) of 7-methoxy-3-methyl-2,3,4,5-tetrahydro-1H-dibenzo[2,3:6,7]thiepino[4,5-d]azepine (prepared in accordance with Example 6) and 140 ml of 48% aqueous hydrobromic acid is refluxed for 2 hours with stirring and then cooled to 20° C. The precipitated hydrobromide of the 7-hydroxy-3-methyl-2,3,4,5-tetrahydro-1H-dibenzo[2,3:6,7]thiepino[4,5-d]azepine is filtered off and dissolved in 160 ml of 60% aqueous methanol. The solution is made alkaline to phenolphthalein by adding a concentrated ammonia solution, whereupon the free 7-hydroxy-3-methyl-2,3,4,5-tetrahydro-1H-dibenzo[2,3:6,7]thiepino[4,5-d]azepine crystallises out. After recrystallisation from acetonitrile, the product melts at 216°-218° C.

For conversion into the methanesulphonate, 9.3 g (0.3 mole) of the base is dissolved in 380 ml of acetone and the resultant solution is treated, with stirring, with 2.88 g (0.03 mole) of methanesulphonic acid, whereupon the 7-hydroxy-3-methyl-2,3,4,5-tetrahydro-1H-dibenzo[2,3:6,7]thiepino[4,5-d]azepine methanesulphonate with a melting point of 282°-286° C. crystallises out.

EXAMPLE 8

A mixture of 18.6 g (0.05 mole) of 7-bromo-3-methyl-2,3,4,5-tetrahydro-1H-dibenzo[2,3:6,7]thiepino[4,5-d]azepine (prepared in accordance with Example 6), 10.7 g (0.12 mole) of copper(I) cyanide in 20 ml of dimethyl formamide is heated, with stirring, in a nitrogen atmosphere to 180° C. The mixture is thereafter cooled to 30° C., diluted with 100 ml of methylene chloride and extracted with 50 ml of a 50% aqueous solution of ethylenediamine. The organic phase is subsequently separated, washed with water, dried over sodium sulphate, and concentrated. The crystalline residue, 7-cyano-3-methyl-2,3,4,5-tetrahydro-1H-dibenzo[2,3:6,7]-thiepino[4,5-d]azepine, melts at 154°-157° C. after recrystallisation from hexane/ethyl acetate.

For conversion into the methanesulphonate, 9.6 g (0.03 mole) of the base is dissolved in acetone and the solution is treated with 2.88 g (0.03 mole) of methanesulphonic acid, whereupon the 7-cyano-3-methyl-2,3,4,5-tetrahydro-1H-dibenzo[2,3:6,7]thiepino[4,5-d]azepine-methanesulphonate with a melting point of 247°-250° C. crystallises out.

EXAMPLE 9

With stirring, 12.2 g (0.075 mole) of octanoyl chloride are added dropwise in the course of 15 minutes to a solution of 16.9 g (0.05 mole) of 2,3,4,5-tetrahydro-1H-dibenzo[2,3:6,7]thiepino[4,5-d]azepine-3-propanol in 50 ml of abs. pyridine, the temperature being kept between 0° and 5° C. The reaction mixture is subsequently stirred for 20 hours at room temperature and then poured onto ice-water and extracted with ether. The organic phase is separated, washed with water, dried over sodium sulphate and completely evaporated to dryness, leaving 3-octanoyloxypropyl-2,3,4,5-tetrahydro-1H-dibenzo[2,3:6,7]thiepino[4,5-d]azepine as oily residue.

The crude base (21.5 g) is dissolved in 150 ml of acetone and to the solution was added 4.2 g (0.047 mole) of anhydrous oxalic acid in 22 ml of abs. alcohol, whereupon 3-oxtanoyloxypropyl-2,3,4,5-tetrahydro-1H-dibenzo[2,3:6,7]thiepino[4,5-d]azepine oxalate crysallises out. Melting point after recrystallisation from abs. ethanol: 157°-162° C.

The following compound can be prepared in analogous manner:
3-acetoxypropyl-2,3,4,5-tetrahydro-1H-dibenzo[2,3:6,7]thiepino[4,5-d]azepine, starting from 16.9 g (0.05 mole) of 2,3,4,5-tetrahydro-1H-dibenzo[2,3:6,7]-thiepino[4,5-azepine-2-propanol in 50 ml of abs. pyridine and 5.9 g (0.75 mole) of acetyl chloride.

EXAMPLE 10

To 75 ml of a 7.4% solution of ethylamine in abs. ethanol (corresponding to 0.012 mole) are added 3.25 g (0.025 mole) of diisopropyl ethylamine, 50 ml of abs. ethanol and 4.5 g (0.01 mole) of 10,11-bis-[2-(methylsulphonyloxy)ethyl]-dibenzo[b,f[thiepine (prepared in accordance with Example 5) and the mixture is heated in a closed tube for 20 hours to 80°-90° C. After it has cooled, the reaction mixture is rinsed in a separating funnel together with 250 ml of methylene chloride and extracted in succession with 50 ml of 2N sodium hydroxide solution and 50 ml of water. The methylene chloride solution is concentrated in a water jet vacuum and the crude 3-ethyl-2,3,4,5-tetrahydro-1H-dibenzo[2,3:6,7]thiepino[4,5-d]azepine is converted in the following manner into the hydrochloride: 3.1 g of the residual viscous brown oil is dissolved in 25 ml of methylene chloride and the solution is treated with 3 ml of a 4N ethereal hydrogen chloride solution. The 3-ethyl-2,3,4,5-tetrahydro-1H-dibenzo[2,3:6,7]thiepino[4,5-d]azepine hydrochloride is precipitated with ether, collected with suction, and recrystallised once from ethanol/ether; melting point of the methanesulphonate: 212°-214° C.

EXAMPLE 11

With stirring, a suspension of 32.1 g (0.1 mole) of 3-methyl-1,5-dihydro-2H-dibenzo[2,3:6,7]thiepino[4,5-d]azepine-2,4(3H)-dione in 500 ml of abs. diethyl ether are added, in a nitrogen atmosphere, to a suspension of 14.6 g (0.38 mole) of lithium aluminium hydride in 1 liter of abs. diethyl ether. During the addition the temperature is kept at 20°-30° C. Thereafter the reaction mixture is refluxed for 15 hours and then cooled to 0°-5° C. Excess lithium aluminium hydride is decomposed by the cautious dropwise addition of 75 ml of ethyl acetate and subsequently of 150 ml of water. The organic phase is separated and extracted repeatedly with 5% methanesulphonic acid. The acid extracts are made alkaline to phenolphthalein with conc. ammonia and crude 3-methyl-2,3,4,5-tetrahydro-1H-dibenzo[2,3:6,7]thiepino[4,5-d]azepine precipitates as an oil. The crude base is extracted with ether and the organic phase is separated, washed with water, dried over sodium sulphate and then evaporated completely to dryness. The residue is dissolved in 50 ml of petroleum ether and cooled to 0° C., whereupon the pure base with a melting point of 83°-86° C. crystallises out. Melting point of the methanesulphonate: 256°-258° C.

The starting material, 3-methyl-1,5-dihdro-2H-dibenzo[2,3:6,7]thiepino[4,5-d]azepine-2,4(3H)-dione can be prepared as follows:

With stirring, a solution of 28.5 g (0.11 mole) of tetrabutylammonium hydroxide in 45 ml of water is added dropwise in a nitrogen atmosphere and in the course of 30 minutes to a solution of 30.7 g (0.1 mole) of 1,5-dihydro-2H-dibenzo[2,3:6,7]thiepino[4,5-d]azepine-2,4(3H)-dione (prepared in accordance with the particulars of Example 6) and 16.6 g (0.12 mole) of methyl iodide in 1 liter of methylene chloride, and the temperature rises from 20° to 25° C. Thereafter the reaction mixture is further stirred for 5 hours at room temperature and then diluted with 250 ml of water. The organic phase is then separated, washed with water, dried over sodium sulphate, and completely evaporated to dryness. The crystalline residue is stirred with 50 ml of abs. ethanol, then collected with suction, and washed with abs. ethanol. The product, 3-methyl-1,5-dihydro-2H-dibenzo[2,3:6,7]thiepino[4,5-d]azepine-2,4(3H)-dione, melts at 216°-222° C. after drying.

EXAMPLE 12

With stirring and excluding moisture, a suspension of 1.14 g (0.03 mole) of lithium aluminium hydride in 75 ml of abs. diethyl ether is introduced slowly in a nitrogen atmosphere to an ice-cooled solution of 4 g (0.03 mole) of aluminium chloride in 100 ml of abs. diethyl ether in such a manner that the reaction temperature does not exceed 5° C. Thereafter a suspension of 2.93 g (0.01 mole) of 1,3,4,5-tetrahydro-2H-dibenzo[2,3:6,7]-thiepino[4,5-d]azepine-2-one in 50 ml of abs. diethyl ether is added and the mixture is refluxed for 24 hours. After cooling to 0°-5° C., excess aluminium hydride is decomposed cautiously by the dropwise addition of 10 ml of water. The organic phase is then separated, washed with two 30 ml portions of water, dried over sodium sulphate and concentrated, to give 2,3,4,5-tetrahydro-1H-dibenzo[2,3:6,7]thiepino[4,5-d]azepine as residue, which melts at 142°-143° C. after recrystallisation from methanol. Melting point of the methanesulphonate: 305°-307° C.

The starting material, 1,3,4,5-tetrahydro-2H-dibenzo[2,3:6,7]azepin-2-one, can be prepared as follows:

With stirring, 198 g (0.5 mole) of 10,11-bis-(bromomethyl)-dibenzo[b,f]thiepine are dissolved in a nitrogen atmosphere at 50° C. in 2.5 liters of acetonitrile. To this solution is added in the course of 10 minutes a solution of 59 g of sodium cyanide in 180 ml of distilled water, the internal temperature being kept at 50° C. by weak cooling. The reaction mixture is further stirred for 30 minutes at this temperature and then 1.5 liters of ice-water are introduced, whereupon dibenzo[b,f]thiepine-10,11-diacetonitrile crystallises out. The grey crystals are collected with suction, washed with water, then with acetonitrile, and subsequently dried in vacuo at 60° C. Melting point: 205°-207° C.

With stirring, 145 g (0.5 mole) of dibenzo[b,f]thiepine-10,11-diacetonitrile are dissolved in 2.75 liters of methylene chloride. While cooling with ice, dry hydrogen bromide is introduced into this solution at 5°-7° C. in the course of 30 minutes and after a time yellow crystals fall out of the reaction mixture. The flow of hydrogen bromide is subsequently stopped and the batch is stirred for a further 30 minutes at 5°-7° C. Approximately half of the solvent is then distilled off from the reaction mixture in vacuo. The residual crystal slurry is collected with suction, well washed with methylene chloride, and the yellow crystals are dried under reduced pressure at 60° C. The resultant 2-amino-4-bromo-1H-dibenzo[2,3:6,7]thiepino[4,5-d]azepine hydrobromide is further processed as crude product.

With stirring, 90 g (0.2 mole) of the above hydrobromide, 1.5 liters of dimethyl formamide and 1.3 liters of water are refluxed for 2 hours in a nitrogen atmosphere. The reaction mixture is then diluted with 800 ml of water at 90°-100° C. and then cooled with ice cooling to 5° C., when 1,5-dibenzo-2H-dibenzo[2,3:6,7]-thiepino[4,5-d]azepine-2,4(3H)-dione crystallises out. The crystals are collected with suction and well washed with water and acetone. After drying at 100° C. under reduced pressure, the crude product melts at 253+−256° C. With stirring and while keeping the temperature at 20°-30° C., a suspension of 61.4 g (0.2 mole) of 1,5-dihydro-2H-dibenzo[2,3:6,7]thiepino[4,5-d]azepine-2,4(3H)-dione in 200 ml of abs. diethyl ether is added in a nitrogen atmosphere and in the course of 30 minutes to a suspension of 22.8 g (0.6 mole) of lithium aluminium hydride in 3.5 liters of abs. diethyl ether and 350 ml of abs. tetrahydrofuran. The reaction mixture is subsequently refluxed for 24 hours and then cooled to 0°-5° C. Excess lithium aluminium hydride is cautiously decomposed by the dropwise addition of 150 ml of ethyl acetate and then of 300 ml of water. The organic phase is separated, washed firstly with 2N hydrochloric acid and then repeatedly with water, dried over sodium sulphate and then completely evaporated to dryness, leaving as residue 1,3,4,5-tetrahydro-2H-dibenzo[2,3:6,7]thiepino[4,5-d]azepin-2-one with a melting point of 195°-198° C.

EXAMPLE 13

With stirring, 8.38 g (0.03 mole) of 2,3,4,5-tetrahydro-1H-dibenzo[2,3:6,7]thiepino[4,5-d]azepine are dissolved in 6 ml of 85%. formic acid at 40°-50° C. To this solution are then added 2.4 ml of 35% formaldehyde solution and the mixture is then stirred for a further 12 hours at an internal temperature of 95°-100° C. The reaction mixture is then cooled to 20° C., diluted with 100 ml of water, and this solution is made alkaline to phenolphthalein with conc. ammonia, whereupon crude 3-methyl-2,3,4,5-tetrahydro-1H-dibenzo[2,3:6,7]thiepino[4,5-d]azepine precipitates as an oil. The crude base is extracted with ether, the organic phase separated, washed twice with water, dried over sodium sulphate and evaporated completely to dryness. The base is then converted as follows into the methanesulphonate:

The crude base (8.4 g) is dissolved in acetone and the solution is treated cautiously with 2.6 g of methanesulphonic acid, whereupon the 3-methyl-2,3,4,5-tetrahydro-1H-dibenzo[2,3:6,7]thiepino[4,5-d]azepine methanesulphonate crystallises out.

Melting point: 256°-258° C. after recrystallisation from abs. ethanol.

EXAMPLE 14

With stirring, 8.38 g (0.03 mole) of 2,3,4,5-tetrahydro-1H-dibenzo[2,3:6,7]thiepino[4,5-]azepine are dissolved in 80 ml of 50% acetic acid. To this solution are then added all at once 8.16 g (0.08 mole) of acetic anhydride and the reaction mixture is allowed to stand for 12 hours at room temperature. The reaction mixture is subsequently completely evaporated to dryness by rotary evaporation. The residue is dissolved in ether and the ethereal solution washed once with 2N sodium hydroxide solution and twice with water. After it has been dried over sodium sulphate, the ethereal solution is completely evaporated to dryness. The residue, 3-acetyl-2,3,4,5-tetrahydro-1H-dibenzo[2,3:6,7]thiepino[4,5-d]azepine, is a yellow oil. The crude acetyl compound (9.4 g) is dissolved in 150 ml of abs. diethyl ether and this solution is added dropwise in the course of half an hour to a suspension of 1.6 g (0.042 mole) of lithium aluminium hydride in 50 ml of abs. diethyl ether, whereupon the reaction mixture comes to the boil. The reaction mixture is then refluxed for a further 6 hours, cooled to 0°-5° C., and diluted by the dropwise addition fo 40 ml of water. The organic phase is separated, washed with water, dried over sodium sulphate, and completely evaporated to dryness. The oily residue is dissolved in 10 ml of acetone and the solution is cooled to −10° C., whereupon 3-ethyl-2,3,4,5-tetrahydro-1H-dibenzo[2,3:6,7]thiepino[4,5-d]azepine with a melting point of 106°-107° C. crystallises out. The methanesulphonate is prepared by the process described in Example 7; melting point 212°-214° C. (from abs. ethanol).

EXAMPLE 15

The following end product is prepared by proceeding according to Example 12: 2,3,4,5-tetrahydro-1H-thieno[2',3':2,3][1]benzo-thiepino[4,5-d]azepine, m.p. 119°-120° C. (from diethyl ether), starting from 30 g (0.1 mole) of a mixture of 1,3,4,5-tetrahydro-2H-thieno[2',3':2,3][1]benzothiepino[4,5-]azepin-2-one and 1,2,3,5-tetrahydro-4H-thieno[2',3':2,3][1]benzo-thiepino[4,5-d]azepin-4-one.

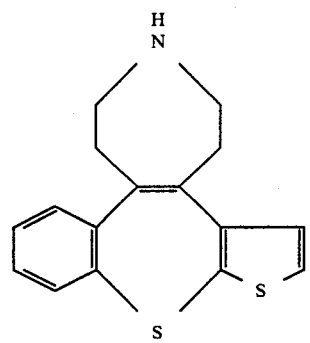

The starting material, the mixture of 1,3,4,5-tetrahydro-2H-thieno[2',3':2,3][1]benzothiepino[4,5-d]azepin-2-one and 1,2,3,5-tetrahydro-4H-thieno[2',3':2,3][1]thiepino[4,5-d]azepin-2-one, can be prepared in a manner analogous to that described in Example 12:
thieno[2,3-b][1]benzothiepine-4,5-diacetoneitrile, m.p. 170°-172° C. (from acetonitrile), starting from 201 g (0.5 mole) of 4,5-bis-(bromomethyl)-thieno[2,3-b][1]benzothiepine;
a mixture of 2-amino-4-bromo-1H-thieno[2',3':2,3][1-]benzothiepino[4,5-d]azepine-hydrobromide and 4-amino-2-bromo-5H-thieno[2',3':2,3][1]benzothiepino[4,5-d]azepine hydrochloride as crude product, starting from 147 g (0.5 mole) of thienol[2,3-b][1]benzothiepine-4,5-diacetonitrile;
1,5-dihydro-2H-thieno[2',3':2,3][1]benzothiepino[4,5-d]azepine-2,4(3H)-dione, m.p. 215°-218° C. (from methanol), and starting from a mixture of 92 g (0.2 mole) of 2-amino-4-bromo-1H-thieno[2',3':2,3][1]benzothiepino[4,5-d]azepine-hydrobromide and 4-amino-2-bromo-5H-thieno[2',3':2,3][1]benzothiepino[4,5-d]azepine-hydrobromide:
a mixture of 1,3,4,5-tetrahydro-2H-thieno[2',3':2,3][1-]benzothiepino[4,5-d]azepin-2-one and 1,2,3,5-tetrahydro-4H-thieno[2',3':2,3][1]benzothiepino[4,5-d]azepin-4-one, crude product, starting from 62.6 g (0.2 mole) of 1,5-dihydro-2H-thieno[2',3':2,3][1]benzothiepino[4,5-d]azepine-2,4(3H)-dione.

EXAMPLE 16

The following end product is prepared in accordance with the procedure of Example 13:
3-methyl-2,3,4,5-tetrahydro-1H-thieno[2',3':2,3][1]benzothiepino [4,5-d]azepine as crude product; melting point of the methanesulphonate 208°-209° C. (from abs. ethanol), starting from 14,3 g (0.05 mole) 2,3,4,5-tetrahydro-1H-thieno[2',3':2,3][1]benzothiepino[4,5-d]azepine.

EXAMPLE 17

The following end product is prepared in accordance with the procedure of Example 14:
3-ethyl-2,3,4,5-tetrahydro-1H-thieno[2',3':2,3][1]benzothiepino[4,5-d]azepine, m.p. 127°-129° C. (from acetone); melting point of the methanesulphonate 209°-211° C. (from abs. ethanol), starting from 14.3 g (0.05 mole) of 2,3,4,5-tetrahydro-1H-thieno[2',3':2,3][1]benzothiepino[4,5-d]azepine.

EXAMPLE 18

The following compounds can be prepared in accordance with the procedure of Example 11, using the appropriate starting materials:

3-[3-(dimethylamino)-propyl]-2,3,4,5-tetrahydro-1H-dibenzo[2,3:6,7]thiepino[4,5-d]azepine as crude product; melting point of the dihydrochloride 285°–289° C. with decompos; starting from 39.3 g (0.1 mole) of 3-[3-(dimethylamino)-propyl]-1,5-dihydro-2H-dibenzo[2,3:6,7]thiepino[4,5-d]azepine-2,4(3H)-dione and 14.6 g (0.38 mole) of lithium aluminium hydride in absolute diethyl ether;

3-[3-(dimethylamino)-propyl]-2,3,4,5-tetrahydro-1H-thieno[2',3':2,3][1]benzothiepino[4,5-d]azepine as crude product; melting point of the dihydrochloride 265°–270° C. with decompos.; starting from 39.9 g (0.1 mole) of 3-[3-(dimethylamino)-propyl]-1,5-dihydro-2H-thieno[2',3':2,3][1]benzothiepino[4,5-d]azepine-2,4(3H)-dione and 14.6 g (0.38 mole) of lithium aluminium hydride in absolute diethyl ether;

3-[3-(dimethylamino)-propyl]-1,2,3,4,5,10-hexanhydro-dibenzo[3,4:6,7]cyclohepta[1,2-d]azepine, m.p. 80°–82° C. (from pentane); melting point of the dihydrochloride approx. 315° C. (with decompos.); starting from 37.4 g (0.1 mole) of 3-[3-(dimethylamino)-propyl]-5,10-dihydro-dibenzo[3,4:6,7]cyclohepta[1,2-d]azepine-2,4-(1H,3H)-dione and 14.6 g (0.38 mole) of lithium aluminium hydride in absolute diethyl ether.

The starting material can be prepared as follows:

(aa) With stirring, a suspension of 2.3 g (0.1 mole) of lithium amide in 6.9 ml of abs. toluene is added dropwise in a nitrogen atmosphere and in the course of 2 hours to a suspension of 30.7 g (0.1 mole) of 1,5-dihydro-2H-dibenzo[2,3:6,7]thiepino[4,5-d]azepine-2,4(3H)-dione in 14.6 g (0.12 mole) of freshly distilled 3-(dimethylamino)-propyl chloride and 600 ml of abs. toluene. The reaction mixture is then refluxed for a further 20 hours and thereafter cooled to room temperature. After addition of 100 ml of water, the organic phase is separated and extracted with three 50 ml portions of 10% methanesulphonic acid. The acid extracts are made alkaline to phenolphthalein with conc. ammonia, whereupon the 3-[3-(dimethylamino)-propyl]-1,5-dihydro-2H-dibenzo[2,3:6,7]thiepino[4,5-d]azepine-2,4(3H)-dione precipitates in crystalline form. Melting point 102°–103° C. after recrystallisation from ether/pentane.

The methanesulphonate is prepared as follows:

The base (30 g) is dissolved in 75 ml of acetone and treated cautiously with 7.3 g (0.076 mole) of methanesulphonic acid, whereupon the 3-[3-(dimethylamino)-propyl]-1,5-dihydro-2H-dibenzo[2,3:6,7]thiepino[4,5-d]azepine-2,4(3H)-dione methanesulphonate crystallises out. Melting point 270°–275° C. after recrystallisation from methanol.

The following compounds can be prepared in analogous manner:

(bb) 3-[3-(dimethylamino)-propyl]-1,5-dihydro-2H-thieno[2',3':2,3][1]benzothiepino[4,5-d]azepine-2,4(3H)-dione, m.p. 117°–119° C. (from acetone); melting point of the hydrochloride 224°–227° C. (from abs. ethanol), starting from 31.2 g (0.1 mole) of 1,5-dihydro-2H-thieno[2',3':2,3][1]benzothiepino[4,5-d]azepine-2,4(3H)-dione, 14.6 g (0.12 mole) of 3-(dimethylamino)-propylchloride and 2.3 g (0.1 mole) of lithium amide; and (cc) 3-[3-(dimethylamino)-propyl]-5,10-dihydro-dibenzo[3,4:6,7]cyclohepta[1,2-d]azepine-2,4(1H,3H)-dione, m.p. 113°–115° C. (from hexane); melting point of the hydrochloride 265°–268° C. (from ethanol), starting from 28.9 g (0.1 mole) of 5,10-dihydro-dibenzo[3,4:6,7]cyclohepta[1,2-d]azepine-2,4(1H,3H)-dione, 14.6 g (0.12 mole) of 3-(dimethylamino)-propylchloride and 2.3 g (0.1 mole) of lithium amide;

5,10-Dihydro-dibenzo[3,4:6,7]cyclohepta[1,2-d]azepine-2,4(1H,3H)-dione is prepared in the same manner as the starting materials of Example 14:

5H-dibenzo[a,d]cycloheptene-10,11-diacetonitrile, m.p. 217°–220° C. (from acetonitrile), starting from 189 g (0.5 mole) of 10,11-bis-(bromomethyl)-5H-dibenzo[a,b]cycloheptene (DOS No. 2,125,654) in 2.5 liters of acetonitrile and 59 g (1.2 mole) of sodium cyanide;

2-amino-4-bromo-1,10-dihydro-dibenzo[3,4:6,7]cyclohepta[1,2-d]azepine hydrobromide, crude product, starting from 135 g (0.5 mole) of 5H-dibenzo[a,b]cycloheptene-10,11-diacetonitrile in 2.75 liters of methylene chloride with dry hydrogen bromide;

5,10-dihydro-dibenzo[3,4:6,7]cyclohepta[1,2-d]azepine-2,4(1H,3H)-dione, m.p. 265° C. (from acetone), starting from 86.5 g (0.2 mole) of 2-amino-4-bromo-1,10-dihydro-dibenzo[3,4:6,7]cyclohepta[1,2-d]azepine hydrobromide, 1.5 liters of dimethyl formamide and 1.3 liters of water.

EXAMPLE 19

Using the appropriate starting material, the following compounds can be prepared in accordance with the particulars of Example 5:

3-butyl-2,3,4,5-tetrahydro-1H-dibenzo[2,3:6,7]thiepino[4,5-d]azepine, m.p. 107°–108° C. (from acetone); m.p. of the methanesulphonate 218°–220° C. (from abs. ethanol), starting from 22.7 g (0.05 mole) of 10,11-bis-[2-(methylsulphonyloxy)-ethyl]dibenzo[b,f]thiepine, 4.4 g (0.06 mole) of n-butylamine and 16.25 g (0.125 mole) of diisopropyl ethylamine in absolute ethanol; 3-allyl-2,3,4,5-tetrahydro-1H-dibenzo[2,3:6,7]thiepino[4,5-d]azepine as crude product; m.p. of the methanesulphonate 225°–227° C. (from abs. ethanol), starting from 22.7 g (0.05 mole) of 10,11-bis-[2-(methylsulphonyloxy)-ethyl]-dibenzo[b,f]thiepine, 3.4 g (0.06 mole) of allylamine and 16.25 g (0.125 mole) of diisopropyl ethylamine in absolute ethanol;

3-propinyl-2,3,4,5-tetrahydro-1H-dibenzo[2,3:6,7]thiepino[4,5-d]azepine as crude product; m.p. of the methanesulphonate 218°–221° C. (from abs. ethanol), starting from 22.7 g (0.05 mole) of 10,11-bis-[2-(methylsulphonyloxy)-ethyl]-dibenzo[b,f]thiepine, 3.3 g (0.06 mole) of propargylamine and 16.25 g (0.125 mole) of diisopropyl ethylamine in absolute ethanol; 3-(cyclopentylmethyl)-2,3,4,5-tetrahydro-1H-dibenzo[2,3:6,7]thiepino[4,5-d]azepine, m.p. 113°–115° C. (from abs. ethanol); m.p. of the methansulphonate 248°–252° C. (from abs. ethanol), starting from 22.7 g (0.05 mole) of 10,11-bis-[2-(methylsulphonyloxy)-ethyl]-dibenzo[b,f]thiepine, 6.0 g (0.06 mole) of (aminomethyl)-cyclopentane and 16.25 g (0.125 mole) of diisopropyl ethylamine in absolute ethanol;

3-(cyclohexylmethyl)-2,3,4,5-tetrahydro-1H-dibenzo[2,3:6,7]thiepino[4,5-d]azepine, m.p. 113°–115° C. (from acetone); m.p. of the methanesulphonate 256°–258° C. (from abs. ethanol), starting from 22.7 g (0.05 mole) of 10,11-bis-[2-methylsulphonyloxy)-ethyl]-dibenzo[b,f]thiepine, 6.7 g (0.06 mole) of (aminomethyl)-cyclohexane and 16.5 g (0.125 mole) of diisopropyl ethylamine in absolute ethanol;

1,2,4,5-tetrahydro-3H-dibenzo[2,3:6,7]thiepino[4,5-d]azepin-3-ethanol, m.p. 157°–159° C. (from acetone); m.p. of the methanesulphonate 194°–198° C. (from abs. ethanol), starting from 22.7 g (0.05 mole) of 10,11-bis-[2-(methylsulphonyloxy)-ethyl]dibenzo[b,f]thiepine, 3.7 g (0.06 mole) of ethanolamine and 16.25 g (0.125 mole) of diisopropyl ethylamine in absolute ethanol;

1,2,4,5-tetrahydro-3H-dibenzo[2,3:6,7]thiepino[4,5-d]azepin-3-propanol, m.p. 120°–132° C. (from acetone); m.p. of the methanesulphonate 181°–183° C. (from abs. ethanol), starting from 22.7 g (0.05 mole) of 10,11-bis-[2-(methylsulphonyloxy)-ethyl]-dibenzo[b,f]thiepine, 4.5 g (0.06 mole) of 3-aminopropanol and 16.25 g (0.125 mole) of diisopropyl ethylamine in absolute ethanol;

3-(3-methoxypropyl)-2,3,4,5-tetrahydro-1H-dibenzo[2,3:6,7]thiepino[4,5-d]azepine as crude product, mp.p of the methanesulphonate 213°–216° C. (from abs. ethanol), starting from 22.7 g (0.05 mole) of 10,11-bis-[2-(methylsulphonyloxy)-ethyl]dibenzo[b,f]thiepine, 5.4 g (0.06 mole) of 3-methoxypropylamine and 16.25 g (0.125 mole) of diisopropyl ethylamine in absolute ethanol;

3-[3-(methylthio)-propyl]-2,3,4,5-tetrahydro-1H-dibenzo[2,3:6,7]thiepino[4,5-d]azepine as crude product, m.p. of the methanesulphonate 212°–214° C. (from abs. ethanol), starting from 22.7 g (0.05 mole) of 10,11-bis-[2-(methylsulphonyloxy)ethyl]-dibenzo[b,f]thiepine, 6.3 g (0.06 mole) of 3-(methylthio)propylamine and 16.25 g (0.125 mole) of diisopropyl ethylamine in absolute ethanol;

3-[2-(methylthio)-ethyl]-2,3,4,5-tetrahydro-1H-dibenzo[2,3:6,7]thiepino[4,5-d]azepine, m.p. 91°–92° C. (from pentane); m.p. of the methanesulphonate 218°–220° C. (from abs. ethanol), starting from 22.7 g (0.05 mole) of 10,11-bis-[2-(methylsulphonyloxy)ethyl]-dibenzo[b,f]-thiepine, 5.5 (0.06 mole) of 2-(methylthio)-ethylamine and 16.25 g (0.125 mole) of diisopropyl ethylamine in absolute ethanol;

7-chloro-3-methyl-2,3,4,5-tetrahydro-1H-dibenzo[2,3:6,7]thiepine[4,5-d]azepine as crude product; m.p. of the hydrochloride 266°–268° C. (from abs. ethanol), starting from 24.5 g (0.05 mole) of 10,11-bis-[2-(methylsulphonyloxy)-ethyl]-2-chloro-dibenzo[b,f]thiepine, 1.85 g of methylamine (0.06 mole) and 16.25 g (0.125 mole) of diisopropyl ethylamine in methanol;

7-chloro-3-(cyclopentylmethyl)-2,3,4,5-tetrahydro-1H-dibenzo[2,3:6,7]thiepin[4,5-d]azepine, m.p. 123°–126° C. (from acetone); m.p. of the methanesulphonate 195°–198° C. (from abs. ethanol), starting from 24.5 g (0.05 mole) of 10,11-bis-[2-methylsulphonyloxy)-ethyl]-2-chloro-dibenzo[b,f]thiepine, 6.7 g (0.06 mole) of (aminomethyl)-cyclopentane and 16.25 g (0.125 mole) of diisopropyl ethylamine is abs. ethanol.

The starting material for the two last mentioned end products can be prepared according to Example 6E:

2-chloro-dibenzo[b,f]thiepine-10,11-diacetonitrile, m.p. 207°–210° C. (from chloroform), starting from 43.1 g (0.1 mole) of 2-chloro-10,11-bis-(bromomethyl)-dibenzo[b,f]thiepine and 11.8 g of sodium cyanide in 500 ml of acetonitrile;

dimethyl 2-chloro-dibenzo[b,f]thiepine-10,11-diacetate, m.p. 111°–113° C. (from methanol), starting from 32.3 g (0.1 mole) of 2-chloro-dibenzo[b,f]thiepine-10,11-diacetonitrile, 400 ml of methanol, 3.8 ml of water and dry hydrogen chloride; 2-chloro-dibenzo[b,f]thiepine-10,11-diethanol, m.p. 152°–154° C. (from diethyl acetate), starting from 38.9 g (0.1 mole) of dimethyl 2-chloro-dibenzo[b,f]thiepine-10,11-diacetate and 7.6 g (0.2 mole) of lithium aluminium hydride in 1 liter of abs. diethyl ether; and 10,11-bis-[2-(methylsulphonyloxy)-ethyl]-2-chloro-dibenzo[b,f]thiepine, m.p. 118°–120° C. (from diethyl ether), starting from 33.3 g (0.1 mole) of 2-chloro-dibenzo[b,f]thiepine-10,11-diethanol, 25.2 g (0.22 mole) of methanesulphonyl chloride in 120 ml of pyridine.

EXAMPLE 20

To a solution of 21.9 g (0.05 mole) of 10,11-bis-[2-methylsulphonyloxy)-ethyl]-dibenzo[b,f]oxepine in 250 ml of absolute ethanol are added 6 g (0.06 mole) of aminomethylcyclopentane and 16.25 g (0.125 mole) of diisopropyl ethylamine and the reaction mixture is refluxed for 18 hours. The crystals which precipitate after cooling with an ice bath are collected by suction and washed with a small amount of isopropanol and pentane. The crystalline product is 3-(cyclopentylmethyl)-2,3,4,5-tetrahydro-1H-dibenzo[2,3:6,7]oxepino[4,5-d]-azepine with a melting point of 99°–101° C. Melting point of the methanesulphonate: 280° C. with decomposition.

1,2,4,5-Tetrahydro-3H-dibenz[2,3:6,7]oxepino[4,5-d]azepine-3-propanol with a melting point of 59°–61° C. (recrystallisation from pentane) can be obtained in analogous manner starting from 21.9 g (0.05 mole) of 10,11-bis-[2-(methylsulphonyloxy)-ethyl]-dibenz[b,f]oxepine, 4.5 g (0.06 mole) of 3-aminopropanol and 16.25 g (0.125 mole) of diisopropyl ethylamine in absolute ethanol. Melting point of the methanesulphonate: 188°–192° C. (recrystallisation from abs. ethanol).

EXAMPLE 21

With stirring, 27.6 g (0.1 mole) of 3-methyl-1,2,3,4,5,10-hexahydrodibenz[b,f]azepino[4,5-d]azepine are dissolved in a mixture of 130 ml of hexametapol and 130 ml of absolute toluene. A suspension of 7.8 g (0.2 mole) of sodium amide in 24 ml of absolute toluene is added dropwise to this solution in the course of 15 minutes while keeping the temperature at 18°–20° C. by gentle cooling. A dry flow of nitrogen is simultaneously passed through the reaction solution in order to expel the ammonia which has formed. When the dropwise addition is complete, stirring is continued for 30 minutes and then a solution of 14.2 g (0.1 mole) of methyl iodide in 100 ml of abs. toluene is added dropwise in the course of 15 minutes while continuing to keep the temperature at 18°–20° C. by cooling with ice. The reaction mixture is stirred for a further 15 minutes and then poured slowly into a mixture of 2 liters of water and 400 ml of toluene. The organic phase is separated and the aqueous phase is extracted with toluene. The combined organic phases are washed with water, dried over potassium carbonate and completely evaporated to dryness. The crystallized residual 3,10-dimethyl-1,2,3,4,5,10-hexahydro-dibenz[b,f]azepino[4,5-d]azepine is recrystallised from ethanol and melts at 197°–199° C. The methanesulphonate melts at 231°–233° C. (recrystallisation from ethanol).

The starting material can be obtained as follows in accordance with the procedure described in Example 6K: 5-acetyl-5H-dibenz[b,f]azepine-10,11-diacetonitrile with a melting point of 183°–185° C. (recrystallisation from benzene), starting from 42.1 g (0.1 mole) of 5-acetyl-10,11-bis-(Bromomethyl)-5H-dibenz[b,f]azepine and 11.8 g (0.24 mole) of sodium cyanide in 500 ml of acetonitrile;

dimethyl 5-acetyl-5H-dibenz[b,f]azepine-10,11-diacetate with a melting point of 123°-124° C. (recrystallisation from toluene), starting from 31.3 g (0.1 mole) of 5-acetyl-5H-dibenz[b,f]azepine-10,11-diacetonitrile, 400 ml of methanol, 3.8 ml of water and dry hydrogen chloride;

5-ethyl-5H-dibenz[b,f]azepine-10,11-diethanol with a melting point of 102°-105° C. (recrystallisation from ether), starting from 37.9 g (0.1 mole) of dimethyl 5-acetyl-5H-dibenz[b,f]azepine-10,11-diacetate and 7.6 g of lithium aluminium hydride in 150 ml of abs. tetrahydrofurane;

10,11-bis-[2-(methylsulphonyloxy)-ethyl]-5-ethyl-5H-dibenz[b,f]azepine with a melting point of 140°-143° C. (recrystallisation from toluene), starting from 30.9 g (0.1 mole) of 5-ethyl-5H-dibenz[b,f]azepine-10,11-diethanol and 25.2 g (0.22 mole) of methanesulphonyl chloride in 120 ml of pyridine;

5H-dibenz[b,f]azepine-10,11-diethanol with a melting point of 180°-182° C. (recrystallisation from acetone), starting from 37.9 g (0.1 mole) of dimethyl 5-acetyl-5H-dibenz[b,f]azepine-10,11-diacetate and 7.6 g of lithium aluminium hydride in 1 liter of abs. diethyl ether;

10,11-bis-[2-(methylsulphonyloxy)-ethyl]-5H-dibenz[b,f]azepine with a melting point of 140°-142° C. (recrystallisation from toluene), starting from 28.1 g (0.1 mole) of 5H-dibenz[b,f]azepine-10,11-diethanol and 25.2 g (0.22 mole) of methanesulphonyl chloride in 120 ml of pyridine; 3-methyl-1,2,3,4,5,10-hexahydro-dibenz[b,f]azepino[4,5-d]azepine with a melting point of 121°-124° C. (recrystallisation from methanol), starting from 21.9 g (0.05 mole) of 10,11-bis-[2-methylsulphonyloxy)-ethyl]-5H-dibenz[b,f]azepine, 1.85 g (0.06 mole) of methylamine and 16.25 g (0.125 mole) of diisopropyl ethylamine. Melting point of the methanesulphonate: 263°-266° C. (recrystallisation from abs. ethanol/acetone).

EXAMPLE 22

The following compounds can be obtained using the corresponding starting materials in accordance with Example 6H:

7-chloro-3-methyl-2,3,4,5-tetrahydro-1H-dibenz[2,3:6,7]oxepino[4,5-d]azepine with a melting point of 174°-176° C. (recrystallisation from toluene), starting from 23.6 g (0.05 mole) of 10,11-bis-[2-(methylsulphonyloxy)-ethyl]-2-chlorodibenz[b,f]oxepine, 1.85 g (0.06 mole) of methylamine and 16.25 g of diisopropyl ethylamine in absolute ethanol; melting point of the hydrochloride: 279°-281° C. (recrystallisation from abs. ethanol).

The starting material, 10,11-bis-[2-(methylsulphonyloxy)ethyl]-2-chloro-dibenz[b,f]oxepine, can be obtained in accordance with the procedure of Example 6H as follows:

(a) 2-chloro-dibenz[b,f]oxepine-10,11-diacetonitrile with a melting point of 227°-230° C. (recrystallisation from ethanol), starting from 20.7 g (0.05 mole) of 10,11-bis-(bromomethyl)-2-chloro-dibenz[b,f]oxepine and 5.9 g (0.12 mole) of sodium cyanide in 250 ml of acetonitrile;

crude dimethyl 2-chloro-dibenz[b,f]oxepine-10,11-diacetate (oil), starting from 15.3 g (0.05 mole) of 2chloro-dibenz-[b,f]oxepine-10,11-diacetonitrile, 200 ml of methanol, 1.9 ml of water and dry hydrogen chloride;

crude 2-chloro-dibenz[b,f]oxepine-10,11-diethanol (oil), starting from 18.7 g (0.05 mole) of dimethyl 2-chloro-dibenz[b,f]oxepine-10,11-diacetate and 3.8 g (0.1 mole) of lithium aluminium hydride in 500 ml of diethyl ether; and crude 10,11-bis-[2-(methylsulphonyloxy)-ethyl]-2-chlorodibenz[b,f]oxepine (oil), starting from 15.8 g (0.05 mole) of 2-chloro-dibenz[b,f]oxepine-10,11-diethanol and 12.6 g (0.11 mole) of methanesulphonyl chloride in 60 ml of pyridine.

EXAMPLE 23

The following compounds can be obtained using the corresponding starting materials in accordance with Examples 5 and 6E:

(A) 3-propyl-2,3,4,5-tetrahydro-1H-dibenzo[2,3:6,7]-thiepine[4,6-d]azepine with a melting point of 128°-130° C. (recrystallisation from acetone), starting from 22.7 g (0.05 mole) of 10,11-bis-[2-(methyl-sulphonyloxy)-ethyl]-dibenzo[b,f]thiepine, 3.3 g (0.06 mole) of propylamine and 16.25 g of diisopropyl ethylamine in absolute ethanol. Melting point of the methanesulphonate: 181°-183° C. (recrystallisation from abs. ethanol);

(B) 7-bromo-3-(cyclopentylmethyl)-2,3,4,5-tetrahydro-1H-dibenzo[2,3:6,7]thiepino[4,5-d]azepine with a melting point of 120°-123° C. (recrystallisation from ethanol), starting from 26.7 g (0.05 mole) of 10,11-bis-[2-methylsulphonyloxy)-ethyl]-2-bromo-dibenzo[b,f]thiepine, 6 g (0.06 mole) of (aminomethyl)cyclopentane and 16.25 g (0.125 mole) of diisopropyl ethylamine;

(C) crude 7-bromo-3-ethyl-2,3,4,5-tetrahydro-1H-dibenzo[2,3:6,7]thiepino[4,5-d]azepine, starting from 26.7 g (0.05 mole) of 10,11-bis-[2-methyl-sulphonyloxy)-ethyl]-2-bromo-dibenzo[b,f]thiepine, 2.7 g (0.06 mole) of ethylamine and 16.25 g (0.125 mole) of diisopropyl ethylamine.

EXAMPLE 24

With stirring, a mixture of 19.3 g (0.05 mole) of 7-bromo-3-ethyl-2,3,4,5-tetrahydro-1H-dibenzo[2,3:6,7]-thiepino[4,5-d]azepine (prepared in accordance with Example 4), 10.7 g (0.12 mole) of copper (I) cyanide in 20 ml of dimethyl formamide is heated for 22 hours to 180° C. in a nitrogen atmosphere. The reaction mixture is then cooled to 30° C., diluted with 100 ml of methylene chloride and treated with 50 ml of a 50% aqueous solution of ethylenediamine. The organic phase is then separated, washed with water, dried over sodium sulphate and dried. The residual crystalline 7-cyano-3-ethyl-2,3,4,5-tetrahydro-1H-dibenzo[2,3:6,7]-thiepino[4,5-d]azepine melts at 154°-156° C. after recrystallisation from hexane/ethyl acetate.

For conversion into the methanesulphonate, 10 g (0.03 mole) of base are dissolved in 50 ml of acetone and to this solution are added, with stirring, 2.88 g (0.03 mole) of methanesulphonic acid, whereupon the 7-cyano-3-ethyl-2,3,4,5-tetrahydro-1H-dibenzo[2,3:6,7]-thiepino[4,5-d]azepinemethanesulphonate crystallises out (m.p. 220°-223° C.). 7-Cyano-3-(cyclopentylmethyl)-2,3,4,5-tetrahydro-1H-dibenzo[2,3:6,7]-thiepino[4,5-]azepine with a melting point of 170°-172° C. (recrystallisation from methanol) can be obtained in analogous manner from 22 g (0.05 mole) of 7-bromo-3-(cyclopentylmethyl)-2,3,4,5-tetrahydro-1H-dibenzo[2,3:6,7]thiepino[4,5-d]azepine and 10.7 g (0.12 mole) of copper (I) cyanide in 20 ml of dimethyl formamide. Melting point of the methanesulphonate: 203°-206° C. (recrystallisation from absolute ethanol).

EXAMPLE 25

Tablets containing 0.02 g of the methanesulphonate of 3-methyl-2,3,4,5-tetrahydro-1H-dibenzo[2,3:6,7]-thiepino[4,5-d]azepine are manufactured as follows:

| | |
|---|---|
| methanesulphonate of 3-methyl-2,3,4,5-tetrahydro-1H—dibenzo[2,3:6,7]thiepino[4,5-d]azepine | 200.00 g |
| lactose | 200.80 g |
| potato starch | 354.70 g |
| stearic acid | 10.00 g |
| talc | 200.00 g |
| magnesium stearate | 2.50 g |
| colloidal silica | 32.00 g |
| ethanol | q.s. |

A mixture of the methanesulphonate of 3-methyl-2,3,4,5-tetrahydro-1H-dibenzo[2,3:6,7]thiepino[4,5-d]azepine, the lactose and 194.70 of the potato starch is moistened with an ethanolic solution of the stearic acid and granulated through a sieve. After drying, the remainder of the potato starch, the talc, the magnesium stearate and the colloidal silica is admixed and the mixture is pressed to tablets weighing 0.1 g each, which can be provided, if desired, with breaking notches for a finer adjustement of the dose.

EXAMPLE 26

Coated tablets containing 0.005 g of the methanesulphonate of 3-methyl-7-cyano-2,3,4,5-tetrahydro-1H-dibenzo[2,3:6,7]thiepino[4,5-d]azepine are manufactured as follows:

| Composition (for 10,000 coated tablets) | |
|---|---|
| methanesulphonate of 3-methyl-7-cyano-2,3,4,5-tetrahydro-1H—dibenzo[2,3:6,7]thiepino[4,5-d]azepine | 50.00 g |
| lactose | 175.90 g |
| stearic acid | 10.00 g |
| colloidal silica | 56.60 g |
| talc | 165.00 g |
| potato starch | 20.00 g |
| magnesium stearate | 2.50 g |
| saccharose (crystals) | 502.28 g |
| shellack | 6.00 g |
| gum arabic | 10.00 g |
| colourant | 0.22 g |
| titanium dioxide | 1.50 g |
| ethanol | q.s. |

Granules are prepared from the methanesulphonate of 3-methyl-7-cyano-2,3,4,5-tetrahydro-1H-dibenzo[2,3:6,7]thiepino[4,5-d]azepine, the lactose and an ethanolic solution of the stearic acid. After drying, these granules are mixed with the colloidal silica, the talc, the potato starch and the magnesium stearate and pressed to coated tablet cores. These cores are then coated with a concentrated syrup of the saccharose, the shellack, the gum arabic, the colourant and the titanium dioxide, and dried, giving coated tablets weighing 0.100 g each.

EXAMPLE 27

Capsules containing 0.02 g of the hydrochloride of 3-methyl-2,3,4,5-tetrahydro-1H-dibenzo[2,3:6,7]oxepino[4,5-d]azepine are manufactured as follows:

| Composition (for 1000 capsules) | |
|---|---|
| hydrochloride of 3-methyl-2,3,4,5-tetrahydro-1H—dibenzo[2,3:6,7]oxepino[4,5-d]azepine | 20.00 g |
| lactose | 253.00 g |
| gelatin | 2.00 g |
| corn starch | 10.00 g |
| talc | 15.00 g |
| water | q.s. |

The hydrochloride of 3-methyl-2,3,4,5-tetrahydro-1H-dibenzo[2,3:6,7]oxepino4,5-d]azepine is mixed with the lactose and the mixture is uniformly moistened with an aqueous solution of the gelatin and granulated through an appropriate sieve (for example a sieve having a maximum mesh size of 1.5 mm). The granules are mixed with the dried corn starch and the talc and packed into hard gelatin capsules (size 1).

EXAMPLE 28

An aqueous injection solution containing 0.01 g/ml of the methanesulphonate of 3-methyl-2,3,4,5-tetrahydro-1H-dibenzo[2,3:6,7]thiepino[4,5-d]azepine is prepared as follows:

| Composition (for 1000 capsules) | |
|---|---|
| methanesulphonate of 3-methyl-2,3,4,5-tetrahydro-1H—dibenzo[2,3:6,7]thiepino[4,5-d]azepine | 10.00 g |
| water | q.s. |

Ampoules are filled with a solution of the methanesulphonate of 3-methyl-2,3,4,5-tetrahydro-1H-dibenzo[2,3:6,7]thiepino[4,5-d]azepine in 1000 ml of water and sterilised. An ampoule contains a 1% solution of the active substance.

We claim:

1. An azatetracyclic compound of the formula

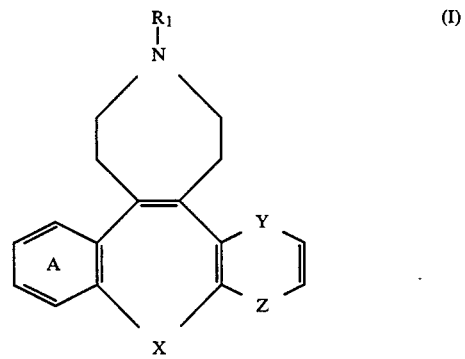

wherein $R_1$ represents hydrogen, lower alkyl, cycloalkyl-lower alkyl of not more than 10 carbon atoms, lower alkenyl, lower alkynyl, (di-lower alkylamino)-lower alkyl, hydroxy lower alkyl, alkoxy lower alkyl, alkanoyloxy lower alkyl having 4 to 11 carbon atoms, lower alkylthio-lower alkyl, phenyl-lower alkyl, phenyl-lower alkyl substituted by halogen with an atomic number up to 35, lower alkyl, lower alkoxy, methylenedioxy, and trifluoromethyl, or lower alkanoyl, the ring A is unsubstituted or substituted by halogen with an atomic number up to 35, lower alkyl, hydroxyl, lower alkoxy, alkanoyloxy having 1-3 carbon atoms, lower alkylthio, trifluoromethyl or cyano, X represents O, S, methylene, a direct bond or a divalent radical of the partial formula

 (Ia)

in which R₃ represents hydrogen or lower alkyl, and one of the radicals Y and Z represents vinylene or S and the other represents a direct bond, and the acid addition salts thereof.

2. The azatetracyclic compound of the formula I according to claim 1, wherein R₁ represents hydrogen, lower alkyl, cycloalkyl-lower alkyl of not more than 8 carbon atoms, lower alkenyl, lower alkynyl, (di-lower alkylamino)-lower alkyl, hydroxy-lower alkyl, lower alkoxy-lower alkyl, alkanoyloxy-lower alkyl having 4 to 11 carbon atoms, lower alkylthio-lower alkyl or phenyl-lower alkyl, and the ring A is unsubstituted or monosubstituted by halogen with an atomic number up to 35, lower alkyl, hydroxy, lower alkoxy, alkanoyloxy having 1 to 3 carbon atoms, lower alkylthio, trifluoromethyl or cyano, X represents O, S, methylene, a direct bond or the divalent radical of the formula

 (Ia)

in which R₃ represents hydrogen or lower alkyl, and one of the radicals Y and Z represents vinylene or S and the other represents a direct bond, and the pharmaceutically acceptable acid addition salts thereof.

3. The azatetracyclic compound of the formula I according to claim 1, wherein R₁ represents hydrogen, lower alkyl, cycloalkyl-lower alkyl of 4 to 8 carbon atoms, lower alkenyl, lower alkynyl, (di-lower alkylamino)-lower alkyl, hydroxy-lower alkyl, lower alkoxy-lower alkyl, alkanoyloxy-lower alkyl having 4–11 carbon atoms, lower alkylthio-lower alkyl or phenyl-lower alkyl, the ring A is unsubstituted or substituted by halogen with an atomic number up to 35, lower alkyl, hydroxy, lower alkoxy, alkanoyloxy having 1 to 3 carbon atoms, lower alkylthio, trifluoromethyl or cyano, X represents O, S, methylene, a direct bond or the divalent radical of the partial formula Ia

 (Ia)

in which R₃ represents hydrogen or lower alkyl of not more than 4 carbon atoms, and one of the radicals Y and Z represents vinylene or S and the other represents a direct bond, and the pharmaceutically acceptable acid addition salt thereof.

4. The azatetracyclic compound of the formula I according to claim 1, wherein R₁ represents hydrogen, lower alkyl, cycloalkyl-lower alkyl of 4 to 8 carbon atoms, lower alkenyl, lower alkynyl, (di-lower alkylamino)-lower alkyl, hydroxy-lower alkyl, lower alkoxy-lower alkyl, alkanoyloxy-lower alkyl having 4 to 11 carbon atoms, lower alkylthio-lower alkyl or phenyl-lower alkyl, the ring A is unsubstituted or substituted by chlorine, bromine, methyl, hydroxy, methoxy, methylthio or cyano, X represents O, S, methylene or a divalent radical of the partial formula Ia

 (Ia)

in which R₃ represents hydrogen, methyl or ethyl, and Y represents a direct bond and Z represents vinylene or S and the pharmaceutically acceptable acid addition salts thereof.

5. A compound according to claim 1 which 3-Methyl-2,3,4,5-tetrahydro-1H-dibenzo[2,3:6,7]thiepino[4,5-d]azepine, and its pharmaceutically acceptable acid addition salts.

6. A compound according to claim 1 which is 3-Methyl-2,3,4,5-tetrahydro-1H-dibenzo[2,3:6,7]oxepino[4,5-d]azepine, and its pharmaceutically acceptable acid addition salts.

7. A compound according to claim 1 which is 3-Methyl-7-cyano-2,3,4,5-tetrahydro-1H-dibenzo[2,3:6,7]thiepino[4,5-d]azepine, and its pharmaceutically acceptable acid addition salts.

8. A compound according to claim 1 which is 3-Methyl-1,2,3,4,5,10-hexahydro-dibenzo[3,4:6,7]cyclohepta[1,2-d]azepine, and its pharmaceutically acceptable acid addition salts.

9. A compound according to claim 1 which is 3-(2,3,4,5-Tetrahydro-1H-dibenzo[2,3:6,7]thiepino[4,5-d]azepin-3-yl)-propanol, and its pharmaceutically acceptable acid addition salts.

10. A pharmaceutical composition useful in the treatment of states of agitation in a warmblooded animal comprising a therapeutically effective amount of an azatetracyclic compound according to claim 1, or a pharmaceutically acceptable acid addition salt thereof together with a pharmaceutical carrier.

11. A pharmaceutical composition according to claim 10 which contains 3-methyl-2,3,4,5-tetrahydro-1H-dibenzo[2,3:6,7]thiepino[4,5-d]azepine or a pharmaceutically acceptable acid addition salt thereof.

12. A pharmaceutical composition according to claim 10, which contains 3-methyl-2,3,4,5-tetrahydro-1H-dibenzo[2,3:6,7]oxepino[4,5-d]azepine or a pharmaceutically acceptable acid addition salt thereof.

13. A method of treating states of agitation in a warmblooded animal which comprises administering to said animal a therapeutically effective amount of a compound according to claim 1, or a pharmaceutically acceptable acid addition salt thereof.

14. A method according to claim 13 which comprises administering a therapeutically effective amount of 3-methyl-2,3,4,5-tetrahydro-1H-dibenzo[2,3:6,7]-thiepino[4,5-d]azepine, or a pharmaceutically acceptable acid addition salt thereof.

15. A method according to claim 13 which comprises administering a therapeutically effective amount of 3-methyl-2,3,4,5-tetrahydro-1H-dibenzo[2,3:6,7]oxepino[4,5-d]azepine, or a pharmaceutically acceptable acid addition salt thereof.

* * * * *

UNITED STATES PATENT AND TRADEMARK OFFICE
CERTIFICATE OF CORRECTION

PATENT NO. : 4,707,476

DATED : November 17, 1987

INVENTOR(S) : Hans Blattner and Angelo Storni

It is certified that error appears in the above-identified patent and that said Letters Patent is hereby corrected as shown below:

The term of this patent subsequent to January 8, 2002, has been disclaimed.

Signed and Sealed this

Twelfth Day of April, 1988

Attest:

DONALD J. QUIGG

Attesting Officer

Commissioner of Patents and Trademarks